(12) United States Patent
Zhang

(10) Patent No.: US 8,524,742 B2
(45) Date of Patent: Sep. 3, 2013

(54) USE OF 5H-THIOENO(3,4-C)PYRROLE-4,6-DIONE DERIVATIVES AS TUMOR NECROSIS FACTOR INHIBITOR

(75) Inventor: Hesheng Zhang, Tianjin (CN)

(73) Assignee: Tianjin Hemay Bio-Tech Co., Ltd., Tianjin (CN)

( * ) Notice: Subject to any disclaimer, the term of this patent is extended or adjusted under 35 U.S.C. 154(b) by 0 days.

(21) Appl. No.: 13/468,031

(22) Filed: May 9, 2012

(65) Prior Publication Data

US 2012/0220631 A1 Aug. 30, 2012

Related U.S. Application Data

(60) Division of application No. 12/051,941, filed on Mar. 20, 2008, now Pat. No. 8,183,260, which is a continuation of application No. PCT/CN2006/002413, filed on Sep. 15, 2006.

(30) Foreign Application Priority Data

Sep. 27, 2005 (CN) .......................... 2005 1 0015209

(51) Int. Cl.
*A61K 31/407* (2006.01)

(52) U.S. Cl.
USPC .......................................... 514/321; 546/198

(58) Field of Classification Search
USPC .......................................... 514/321; 546/198
See application file for complete search history.

(56) References Cited

PUBLICATIONS

Aragon-Ching et al. "Thalidomide analogues . . . " Recent Pat Anticancer Drug Discov. 2(2): 167-174 (2007).*
Crohn's Disease "Health and disease " p. 1, (2012).*
Srinivasan et al. "Thalidomide and . . . " The Cochrane Library p. 1-13 (2009).*
Makonkawkeyoon et al. "Thalidomide inhibits . . . " Proc. Natl. Acd. Sci. v.90, p. 5984-5978 (1993).*

* cited by examiner

*Primary Examiner* — Celia Chang
(74) *Attorney, Agent, or Firm* — Matthias Scholl P.C.; Matthias Scholl

(57) ABSTRACT

A method of treating or curing a disease caused by or associated with elevated levels of TNF in a patient including administering to the patient 5H-thioeno(3,4-c)pyrrole-4,6-dione derivatives.

11 Claims, No Drawings

US 8,524,742 B2

USE OF 5H-THIOENO(3,4-C)PYRROLE-4,6-DIONE DERIVATIVES AS TUMOR NECROSIS FACTOR INHIBITOR

CROSS-REFERENCE TO RELATED APPLICATIONS

This application is a divisional of U.S. Ser. No. 12/051,941 filed on Mar. 20, 2008, now pending, which is a continuation of International Patent Application No. PCT/CN2006/002413, with an international filing date of Sep. 15, 2006, which is based on Chinese Patent Application No. 200510015209.6, filed on Sep. 27, 2005. The contents of all of the aforementioned Applications, including any intervening amendments thereto, are incorporated herein by reference in their entirety.

BACKGROUND OF THE INVENTION

1. Field of the Invention

This invention relates to 5H-thioeno(3,4-c)pyrrole-4,6-dione derivatives which are active as inhibitors of tumor necrosis factor (TNF) released by cells, the preparation of these derivatives, as well as their application as pharmaceutically-active ingredients.

2. Description of the Related Art

Tumor necrosis factor-alpha (TNFα) is a cytokine, mainly produced by mononuclear macrophages. It causes inflammation, fever, cardiovascular dysfunction, hemorrhage, blood coagulation and a series of acute reactions similar to acute infection and shock when administered to humans and animals. Moreover, excessive or uncontrolled TNFα in animals or humans often indicates one of the following diseases:

1) Endotoxaemia and/or toxic shock syndrome (Tracey et al., Nature 330, 662-4 1987; Hinshaw et al., Circ Shock 30, 279-92 (1990));
2) Cachexia (Dezube et al., Laucet, 335(8690), 662 (1990)); or
3) Adult Respiratory Distress Syndrome (ARDS) (Millar et al., Laucet 2(8665), 712-714 (1989)).

At present, the disease most commonly linked to TNFα released by tumor and host tissue is hypercalcemia, which is closely related to malignant tumors (Calci. Tissue Int. (US) 46(Suppl.), S3-10 (1990)). It has also been observed that immune response is closely related to an increased concentration of TNFα in serum of the patient after bone marrow transplantation (Holler et al., Blood, 75(4), 1011-1016 (1990)).

Fatal hyperacute neurogenic syndrome brainstem-type malaria, which is the most dangerous type of malaria, is also linked to high levels of TNFα in blood. When this kind of malaria occurs, the levels of TNFα in serum are directly related to the disease, which often occurs during an acute attack of malaria in patients (Grau et al., N. Engl. J. Med. 320(24), 1586-91 (1989)).

TNFα also plays an important role in bone resorption diseases including arthritis (Betolinni et al., Nature 319, 516-8 (1986)). TNFα may stimulate bone resorption by stimulating the formation and activation of osteoclast and inhibit the formation of bone, which was shown both by in vitro and in vivo experiments.

TNFα plays an important role in chronic pneumonia, as well. The storage of silicon-containing particles can cause silicosis. Silicosis is a type of progressive respiratory failure, resulting from fibrosis of pulmonary tissues. In an animal pathological model, TNFα antibody can fully block the progress of lung fibrosis in mice caused by silica dust (Pignet et al., Nature, 344:245-7 (1990)). It was also proved that TNFα levels are abnormally high in serum of animals with pulmonary fibrosis caused by silica dust or asbestos dust in animal experiments (Bissonnette et al., Inflammation 13(3), 329-339 (1989)). Pathological research reveals that TNFα levels in pulmonary tissues of patients with pulmonary sarcoidosis is much higher than that of ordinary people (Baughman et al., J. Lab. Clin. Med. 115(1), 36-42 (1990)). This suggests that TNFα inhibitor could have a great significance in the treatment of chronic pulmonary diseases and lung injury.

One reason for inflammation occurring in the patient with reperfusion injury may be abnormal levels of TNFα.

TNFα is regarded as the chief cause inducing tissue injury caused by ischemia (Uadder et al., PNAS 87, 2643-6 (1990)).

Besides, it has been shown that TNFα may start retroviral replication including that of HIV-1 (Duh et al., Proc. Nat. Acad. Sci., 86, 5974-8 (1989)). T-cells need to be activated before HIV invades them. Once the activated T-cells are infected by virus (HIV), those T-cells must remain in an activated state in order for the HIV virus genes are able to express and/or replicate successfully. Cytokines, especially TNFα, play an important role in the process of HIV protein expression or viral replication controlled by T-cells. Inhibition of TNFα production can in turn inhibit HIV replication in T-cells (Poll et al., Proc. Nat. Acad. Sci., 87, 782-5 (1990); Monto et al., Blood 79, 2670 (1990); Poll et al., AIDS Res. Human Retrovirus, 191-197 (1992)).

cAMP can regulate many functions of cells, such as inflammation response, including asthma, and inflammation (Lome and Cheng, Drugs of the futune, 17(9), 799-807, 1992). When inflammation occurs, increased cAMP concentration in white cells inhibits activation of white cells, and then releases inflammation regulatory factors including TNFα so as to exacerbate inflammation in patients. Consequently, the inhibition of TNFα release can alleviate inflammation diseases including asthma.

Yu Yanyan et al, have found that TNFα plays an important role in the process of liver necrosis in patients with viral hepatitis. (Yu Yanyan etc., Chinese Journal of Internal Medicine 1996, 35:28-31). This shows that TNFα inhibitors may play a great role in treatment of chronic hepatic disease and liver injury.

Li Yingxu et al have found that levels of synthesis and secretion of tumor necrosis factors in monocytes in the peripheral blood of patients with chronic hepatic disease increase, which induces secretion of other cytokines (for example, IL-1β, IL-6 and IL-8). All these cytokines including tumor necrosis factors are all together involved in the injury process of hepatocytes (Journal of Qiqihar Medical Colleg, 22(10):1119-1120, 2001). Their study results coincide with the conclusions of Yoshioka, et al. (Hepatology, 1989, 10:769-777) and Wang Xin, et al. (Chinese Journal of Infectious Diseases, 1997, 15(2):85-88). It has also been found that thalidomide, the inhibitor of TNFα, is able to inhibit TNFα secretion of monocytes in the peripheral blood of hepatitis patients, which lays a foundation for the application of TNFα inhibitors to treatment of hepatitis, cirrhosis and liver cancer.

By promoting biosynthesis and release of inflammatory cytokines (Abboud H. E. Kidney Int. 1993, 43: 252-267), increasing expression of cellular adhesion molecules (Egido J. et al, Kidney Int. 1993, 43(suppl 39): 59-64), and stimulating biosynthesis and release of prostaglandin G2 (PGG2) and platelet-activating factor (PAF) (Cammusi G. et al, Kidney Int., 43(suppl 39): 32-36), TNFα may induce aggregation and adhesion of inflammatory cells, increase dilation and permeability of blood capillaries, induce fever, increase the count of neutrophilic granulocytes in blood circulation, and change hemodynamics leading to injury of renal cells. Many studies have suggested that TNFα plays an important role in breakout and deterioration of nephritis.

TNFα regulates the differentiation of B lymphocytes and reinforces the cytotoxicity of natural killer cells (NK), so as to involve in the regulation of immunel functions by means of activation of macrophages and immunological stimulation of proliferation of T-lymphocytes.

Therefore, decreasing TNFα levels and/or increasing cAMP levels constitutes an effective way to treat many inflammatory, infectious, immune or malignant tumor diseases, including but not limited to septic shock, endotoxic shock, hemodynamic shock, septic syndrom, post ischemic reperfusion injury, malaria, mycobacterial infection, meningitis, psoriasis, congestive heart failure, fibrotic disease, cachexia, transplant immune rejection, cancer, autoimmune disease, opportunistic infection in AIDS, rheumatoid arthritis (RA), hepatitis, nephritis, rheumatoid spondylitis, and so on. Accordingly, research and development on small molecule TNFα inhibitors with low toxicity and high efficiency is of great social benefit and has high economic value.

SUMMARY OF THE INVENTION

This invention is directed to 5H-thioeno(3,4-c)pyrrole-4,6-dione derivatives and organic or inorganic salts thereof, preparation methods thereof, and their application as pharmaceutically-active ingredients useful as TNFα release inhibitors in cells.

The 5H-thioeno(3,4-c)pyrrole-4,6-dione derivatives of this invention are encompassed by the general formula (I):

(I)

wherein:
$R^1$ represents H, $C_{1-6}$alkyl, $OR^4$, $OC(O)R^5$, $NO_2$, $NHC(O)R^6$, or $NR^7R^8$;
$R^2$ represents H, halogen atoms, or $C_{1-6}$alkyl;
$R^3$ represents H, methyl, isopropyl, allyl, benzyl, $CH_2CO_2(C_{1-6}$alkyl), or $CH_2(CH_2)_nR^9$;
$R^4$, $R^5$, $R^6$, $R^7$, and $R^8$ represent independently and at each occurrence H, or $C_{1-6}$alkyl;
$R^9$ represents H, $C_{1-6}$alkyl, OH, $OC_{1-6}$alkyl, $NH_2$, $NHC_{1-6}$alkyl, $N(C_{1-6}$ alkyl$)_2$, or $CO_2(C_{1-6}$alkyl); and
n represents 1, 2, 3, or 4.

The $C_{1-6}$alkyl described in this invention may be straight chain, fork chain or cyclic alkyl; a saturated or unsaturated alkyl; and may be substituted by F, OH, COOH, $CO_2(C_{1-4}$ alkyl), $C(O)NH_2$, $C(O)NH(C_{1-4}$alkyl), $C(O)N(C_{1-4}$alkyl$)_2$, $NHC(O)(C_{1-4}$alkyl), $NH_2$, $NH(C_{1-4}$alkyl), $N(C_{1-4}$alkyl$)_2$, $NHC(O)NH_2$, $NHC(NH)NH_2$, $O(C_{1-4}$alkyl), and/or $S(C_{1-4}$alkyl).

Among compounds represented by formula (I), suitable as a pharmaceutically-active ingredients useful as TNFα release inhibitors in cells are those compounds wherein $R^1$ represents H, $CH_3$, $CH_2CH_3$, OH, $OCH_3$, $OCH_2CH_3$, $O_2CCH_3$, $O_2CCH_2CH_3$, $NH_2$, $NHCH_3$, $NHCH_2CH_3$, $N(CH_3)_2$, $NHC(O)H$, $NHC(O)CH_3$, $NHC(O)CH_2CH_3$, or $N(CH_3)C(O)CH_3$; particularly suitable are compounds represented by formula (I) wherein $R^1$ represents H, CH3, OH, $OCH_3$, $NH_2$, $NHCH_3$, $NHCH_2CH_3$, $N(CH_3)_2$, or $NHC(O)CH_3$; and more particularly are compounds represented by formula (I) wherein $R^1$ represents H, $NH_2$, $NHCH_3$, or $N(CH_3)C(O)CH_3$.

Among compounds represented by formula (I), suitable as a pharmaceutically-active ingredients useful as TNFα release inhibitors in cells are those compounds wherein $R^2$ represents H, F, $CH_3$, $CH_2CH_3$, or $CH_2CH_2CH_3$; particularly suitable are compounds represented by formula (I) wherein $R^2$ represents H, F, $CH_3$, or CH2CH3; and more particularly are compounds represented by formula (I) wherein $R^2$ represents H, F, or $CH_3$.

Among compounds represented by formula (I), suitable as a pharmaceutically-active ingredients useful as TNFα release inhibitors in cells are those compounds wherein $R^3$ represents H, $CH_3$, $CH_2CH_3$, $CH_2CH_2CH_3$, isopropyl, allyl, $CH_2CH_2CH_2CH_3$, $CH_2Ph$, $CH_2CH_2OH$, $CH_2CH_2CH_2OH$, $CH_2CH_2CH_2CH_2OH$, $CH_2CH_2OCH_3$, $CH_2CH_2OCH_2CH_3$, $CH_2CO_2CH_3$, $CH_2CO_2CH_2CH_3$ or $CH_2CH_2CO_2CH_2CH_3$; particularly suitable are compounds represented by formula (I) wherein $R^3$ represents H, $CH_3$, $CH_2CH_3$, $CH_2CH_2CH_3$, $CH_2CH_2OH$, $CH_2CH_2CH_2OH$, $CH_2CH_2OCH_3$ or $CH_2CO_2CH_3$; and more particularly are compounds represented by formula (I) wherein $R^3$ represents H, $CH_3$, $CH_2CH_3$, $CH_2CH_2OH$, $CH_2CH_2OCH_3$ or $CH_2CO_2CH_3$.

Among the 5H-thieno(3,4-c)pyrrole-4,6-dione derivatives represented by formula (I), suitable as a pharmaceutically-active ingredients useful as TNFα release inhibitors in cells are, without limitation, the following compounds:

1) 5-(2,6-dioxopiperidin-3-yl)-5H-thieno(3,4-c)pyrrole-4,6-dione

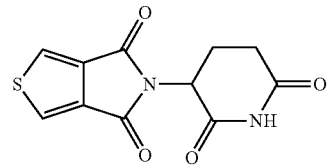 [SMILES: O=C1CCC(N2C(=O)c3cscc3C2=O)C(=O)N1]

2) 5-(3-methyl-2,6-dioxopiperidin-3-yl)-5H-thieno(3,4-c)pyrrole-4,6-dione

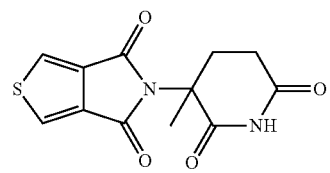 [SMILES: CC1(N2C(=O)c3cscc3C2=O)CCC(=O)NC1=O]

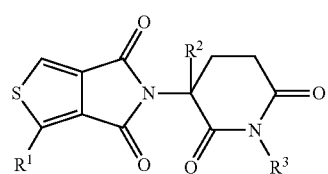

3) 5-(1-methyl-2,6-dioxopiperidin-3-yl)-5H-thieno(3,4-c)pyrrole-4,6-dione

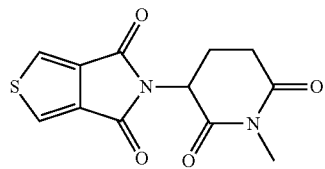

4) 5-(1-ethyl-2,6-dioxopiperidin-3-yl)-5H-thieno(3,4-c)pyrrole-4,6-dione

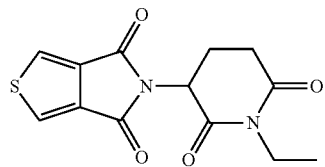 [SMILES: CCN1C(=O)CCC(N2C(=O)c3cscc3C2=O)C1=O]

5) 5-(1-(2-methoxyethyl)-2,6-dioxopiperidin-3-yl)-5H-thieno(3,4-c)pyrrole-4,6-dione

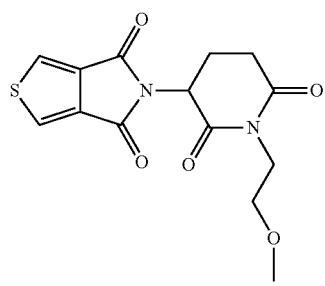 [SMILES: COCCN1C(=O)CCC(N2C(=O)c3cscc3C2=O)C1=O]

6) 5-(1,3-dimethyl-2,6-dioxopiperidin-3-yl)-5H-thieno(3,4-c)pyrrole-4,6-dione

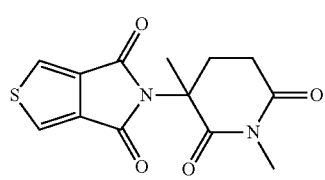 [SMILES: CN1C(=O)CCC(C)(N2C(=O)c3cscc3C2=O)C1=O]

7) 1-nitro-5-(2,6-dioxopiperidin-3-yl)-5H-thieno(3,4-c)pyrrole-4,6-dione

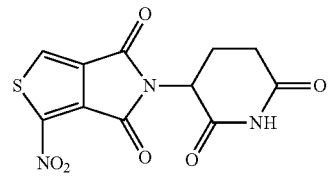 [SMILES: O=C1CCC(N2C(=O)c3csc([N+](=O)[O-])c3C2=O)C(=O)N1]

8) 5-(1-methyl-2,6-dioxopiperidin-3-yl)-1-nitro-5H-thieno(3,4-c)pyrrole-4,6-dione

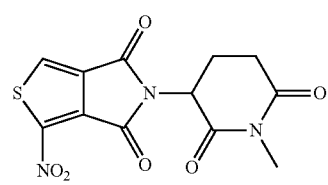 [SMILES: CN1C(=O)CCC(N2C(=O)c3csc([N+](=O)[O-])c3C2=O)C1=O]

9) (±)-5-(3-methyl-2,6-dioxopiperidin-3-yl)-1-nitro-5H-thieno(3,4-c)pyrrole-4,6-dione

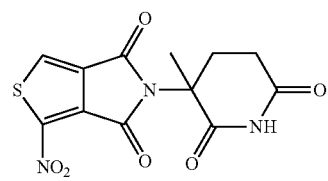 [SMILES: CC1(N2C(=O)c3csc([N+](=O)[O-])c3C2=O)CCC(=O)NC1=O]

10) (R)-5-(3-methyl-2,6-dioxopiperidin-3-yl)-1-nitro-5H-thieno(3,4-c)pyrrole-4,6-dione

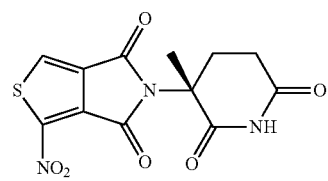 [SMILES: C[C@@]1(N2C(=O)c3csc([N+](=O)[O-])c3C2=O)CCC(=O)NC1=O]

11) (S)-5-(3-methyl-2,6-dioxopiperidin-3-yl)-1-nitro-5H-thieno(3,4-c)pyrrole-4,6-dione

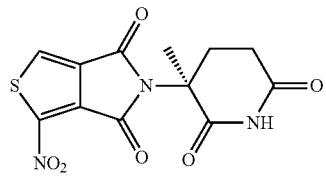 [SMILES: C[C@]1(N2C(=O)c3csc([N+](=O)[O-])c3C2=O)CCC(=O)NC1=O]

12) (R)-5-(3-methyl-2,6-dioxopiperidin-3-yl)-1-amino-5H-thieno(3,4-c)pyrrole-4,6-dione

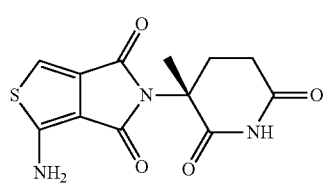 [SMILES: C[C@@]1(N2C(=O)c3csc(N)c3C2=O)CCC(=O)NC1=O]

13) (S)-5-(3-methyl-2,6-dioxopiperidin-3-yl)-1-amino-5H-thieno(3,4-c)pyrrole-4,6-dione

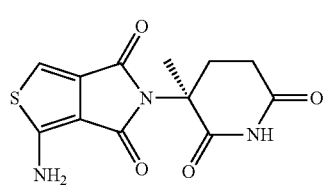 [SMILES: C[C@]1(N2C(=O)c3csc(N)c3C2=O)CCC(=O)NC1=O]

14) (±)-5-(3-methyl-2,6-dioxopiperidin-3-yl)-1-amino-5H-thieno(3,4-c)pyrrole-4,6-dione

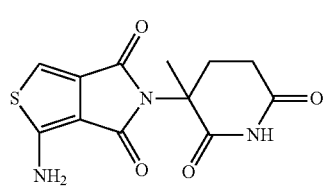

15) (R)-5-(1,3-dimethyl-2,6-dioxopiperidin-3-yl)-1-amino-5H-thieno(3,4-c)pyrrole-4,6-dione

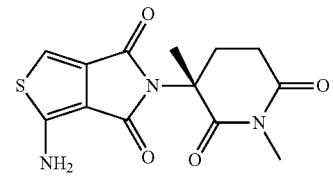 [SMILES: CN1C(=O)CC[C@@](C)(N2C(=O)c3csc(N)c3C2=O)C1=O]

16) (S)-5-(1,3-dimethyl-2,6-dioxopiperidin-3-yl)-1-amino-5H-thieno(3,4-c)pyrrole-4,6-dione

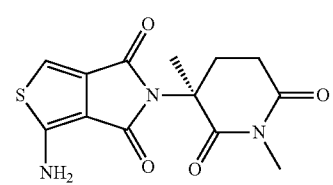 [SMILES: CN1C(=O)CC[C@](C)(N2C(=O)c3csc(N)c3C2=O)C1=O]

17) (±)-5-(1,3-dimethyl-2,6-dioxopiperidin-3-yl)-1-amino-5H-thieno(3,4-c)pyrrole-4,6-dione

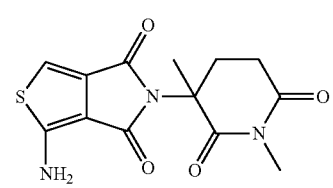 [SMILES: CN1C(=O)CCC(C)(N2C(=O)c3csc(N)c3C2=O)C1=O]

18) (R)-5-(3-methyl-2,6-dioxopiperidin-3-yl)-1-methylamino-5H-thieno(3,4-c)pyrrole-4,6-dione

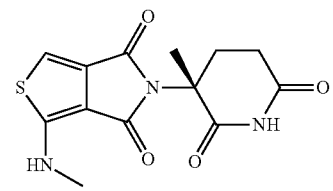 [SMILES: CNc1scc2c1C(=O)N([C@]1(C)CCC(=O)NC1=O)C2=O]

19) (S)-5-(3-methyl-2,6-dioxopiperidin-3-yl)-1-methylamino-5H-thieno(3,4-c)pyrrole-4,6-dione

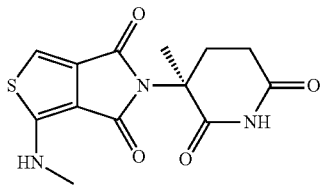 [SMILES: CNc1scc2c1C(=O)N(C1(C)CCC(=O)NC1=O)C2=O]

20) (±)-5-(3-methyl-2,6-dioxopiperidin-3-yl)-1-methylamino-5H-thieno(3,4-c)pyrrole-4,6-dione

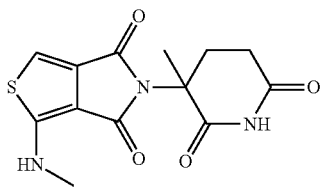

21) (R)-5-(3-methyl-2,6-dioxopiperidin-3-yl)-1-ethylamino-5H-thieno(3,4-c)pyrrole-4,6-dione

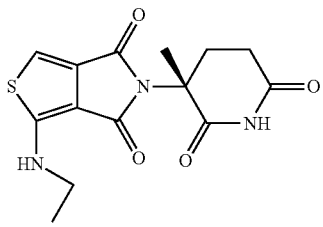 [SMILES: CCNc1scc2c1C(=O)N([C@]1(C)CCC(=O)NC1=O)C2=O]

22) (S)-5-(3-methyl-2,6-dioxopiperidin-3-yl)-1-ethylamino-5H-thieno(3,4-c)pyrrole-4,6-dione

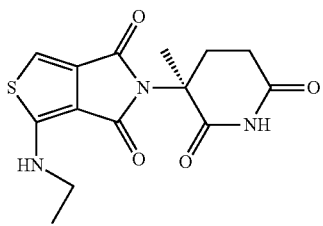 [SMILES: CCNc1scc2c1C(=O)N([C@@]1(C)CCC(=O)NC1=O)C2=O]

23) (±)-5-(3-methyl-2,6-dioxopiperidin-3-yl)-1-ethylamino-5H-thieno(3,4-c)pyrrole-4,6-dione

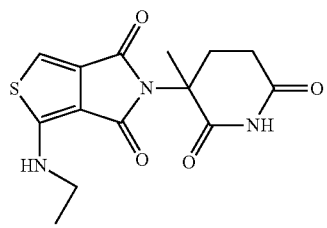 [SMILES: CCNc1scc2c1C(=O)N(C1(C)CCC(=O)NC1=O)C2=O]

24) (R)-5-(3-methyl-2,6-dioxopiperidin-3-yl)-1-dimethylamino-5H-thieno(3,4-c)pyrrole-4,6-dione

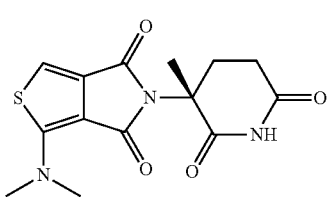 [SMILES: CN(C)c1scc2c1C(=O)N([C@]1(C)CCC(=O)NC1=O)C2=O]

25) (S)-5-(3-methyl-2,6-dioxopiperidin-3-yl)-1-dimethylamino-5H-thieno(3,4-c)pyrrole-4,6-dione

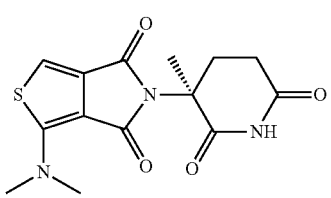 [SMILES: CN(C)c1scc2c1C(=O)N([C@@]1(C)CCC(=O)NC1=O)C2=O]

26) (±)-5-(3-methyl-2,6-dioxopiperidin-3-yl)-1-dimethylamino-5H-thieno(3,4-c)pyrrole-4,6-dione

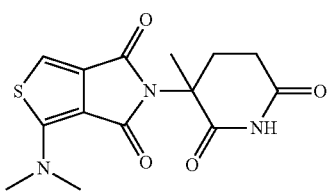 [SMILES: CN(C)c1scc2c1C(=O)N(C1(C)CCC(=O)NC1=O)C2=O]

27) (R)-5-(3-methyl-2,6-dioxopiperidin-3-yl)-1-propylamino-5H-thieno(3,4-c)pyrrole-4,6-dione

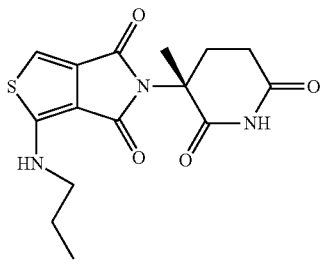 [SMILES: CCCNc1scc2c1C(=O)N([C@]1(C)CCC(=O)NC1=O)C2=O]

28) (S)-5-(3-methyl-2,6-dioxopiperidin-3-yl)-1-propylamino-5H-thieno(3,4-c)pyrrole-4,6-dione

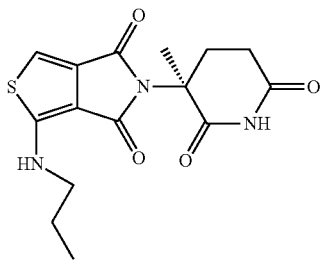 [SMILES: CCCNc1scc2c1C(=O)N([C@@]1(C)CCC(=O)NC1=O)C2=O]

29) (±)-5-(3-methyl-2,6-dioxopiperidin-3-yl)-1-propylamino-5H-thieno(3,4-c)pyrrole-4,6-dione

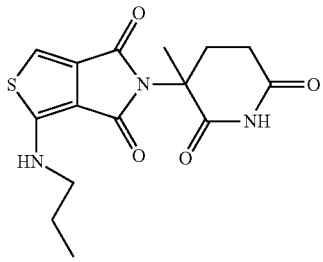 [SMILES: CCCNc1scc2c1C(=O)N(C1(C)CCC(=O)NC1=O)C2=O]

30) (R)-5-(3-methyl-2,6-dioxopiperidin-3-yl)-1-isopropylamino-5H-thieno(3,4-c)pyrrole-4,6-dione

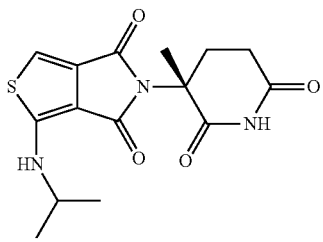 [SMILES: CC(C)Nc1scc2c1C(=O)N([C@]1(C)CCC(=O)NC1=O)C2=O]

31) (S)-5-(3-methyl-2,6-dioxopiperidin-3-yl)-1-isopropylamino-5H-thieno(3,4-c)pyrrole-4,6-dione

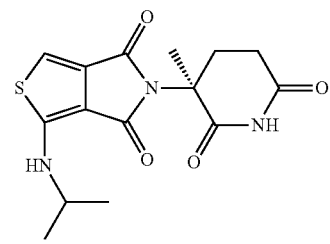 [SMILES: CC(C)Nc1scc2c1C(=O)N([C@@]1(C)CCC(=O)NC1=O)C2=O]

32) (±)-5-(3-methyl-2,6-dioxopiperidin-3-yl)-1-isopropylamino-5H-thieno(3,4-c)pyrrole-4,6-dione

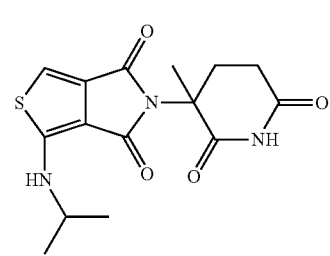 [SMILES: CC(C)Nc1scc2c1C(=O)N(C1(C)CCC(=O)NC1=O)C2=O]

33) (R)-5-(3-methyl-2,6-dioxopiperidin-3-yl)-1-(ethyl(methyl)amino)-5H-thieno(3,4-c)pyrrole-4,6-dione

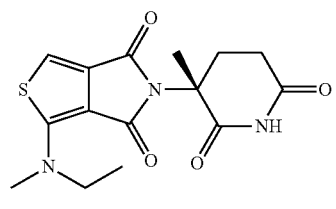 [SMILES: CCN(C)c1scc2c1C(=O)N([C@]1(C)CCC(=O)NC1=O)C2=O]

34) (S)-5-(3-methyl-2,6-dioxopiperidin-3-yl)-1-(ethyl(methyl)amino)-5H-thieno(3,4-c)pyrrole-4,6-dione

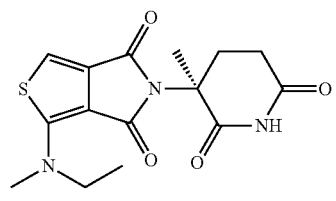

35) (±)-5-(3-methyl-2,6-dioxopiperidin-3-yl)-1-(ethyl(methyl)amino)-5H-thieno(3,4-c)pyrrole-4,6-dione

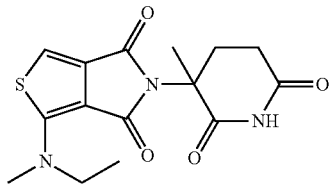 [SMILES: CCN(C)c1scc2c1C(=O)N([C@@]1(C)CCC(=O)NC1=O)C2=O]

36) (R)-5-(3-ethyl-2,6-dioxopiperidin-3-yl)-1-amino-5H-thieno(3,4-c)pyrrole-4,6-dione

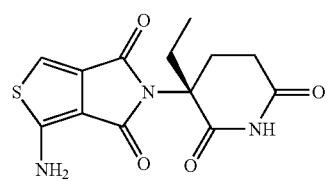 [SMILES: CC[C@@]1(N2C(=O)c3csc(N)c3C2=O)CCC(=O)NC1=O]

37) (S)-5-(3-ethyl-2,6-dioxopiperidin-3-yl)-1-amino-5H-thieno(3,4-c)pyrrole-4,6-dione

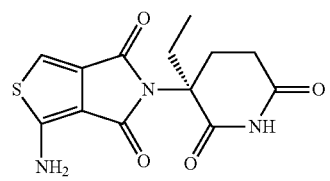

38) (±)-5-(3-ethyl-2,6-dioxopiperidin-3-yl)-1-amino-5H-thieno(3,4-c)pyrrole-4,6-dione

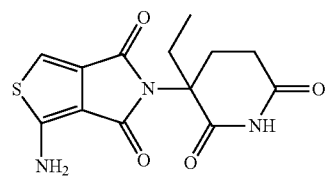

39) (R)-5-(3-methyl-2,6-dioxopiperidin-3-yl)-1-acetamido-5H-thieno(3,4-c)pyrrole-4,6-dione

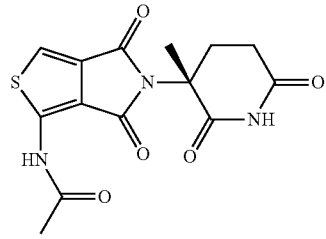 [SMILES: CC(=O)Nc1scc2c1C(=O)N([C@]1(C)CCC(=O)NC1=O)C2=O]

40) (S)-5-(3-methyl-2,6-dioxopiperidin-3-yl)-1-acetamido-5H-thieno(3,4-c)pyrrole-4,6-dione

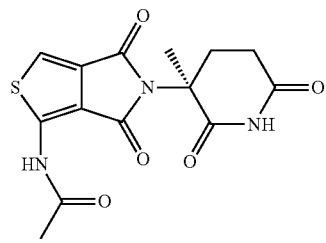 [SMILES: CC(=O)Nc1scc2c1C(=O)N(C1(C)CCC(=O)NC1=O)C2=O]

41) (±)-5-(3-methyl-2,6-dioxopiperidin-3-yl)-1-acetamido-5H-thieno(3,4-c)pyrrole-4,6-dione 42) 5-(1-ethyl-2,6-dioxopiperidin-3-yl)-1-amino-5H-thieno(3,4-c)pyrrole-4,6-dione

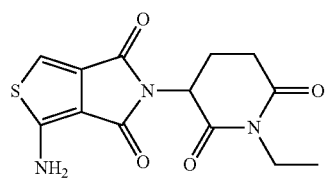

43) 5-(1-(2-hydroxyethyl)-2,6-dioxopiperidin-3-yl)-1-amino-5H-thieno(3,4-c)pyrrole-4,6-dione

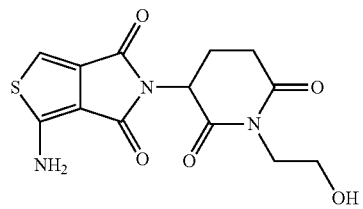 [SMILES: Nc1scc2c1C(=O)N(C1CCC(=O)N(CCO)C1=O)C2=O]

44) 5-(1-ethyl-2,6-dioxopiperidin-3-yl)-1-amino-5H-thieno(3,4-c)pyrrole-4,6-dione

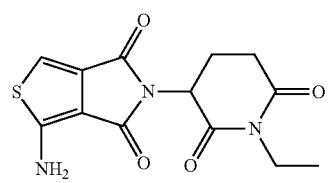 [SMILES: CCN1C(=O)CCC(N2C(=O)c3csc(N)c3C2=O)C1=O]

45) 5-(1-(3-hydroxypropyl)-2,6-dioxopiperidin-3-yl)-1-amino-5H-thieno(3,4-c)pyrrole-4,6-dione

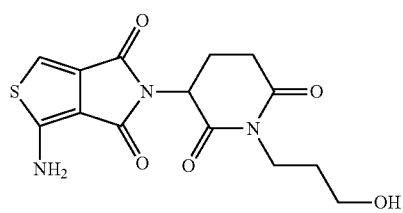 [SMILES: Nc1scc2c1C(=O)N(C1CCC(=O)N(CCCO)C1=O)C2=O]

46) 5-(1-(3-methoxypropyl-2,6-dioxopiperidin-3-yl)-1-amino-5H-thieno(3,4-c)pyrrole-4,6-dione

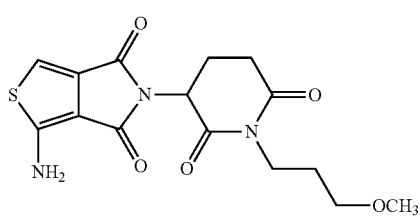 [SMILES: COCCCN1C(=O)CCC(N2C(=O)c3csc(N)c3C2=O)C1=O]

47) 5-(1-propyl-2,6-dioxopiperidin-3-yl)-1-amino-5H-thieno(3,4-c)pyrrole-4,6-dione

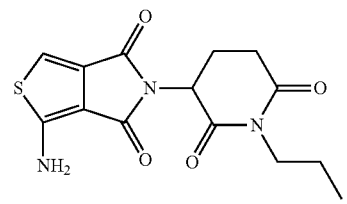 [SMILES: CCCN1C(=O)CCC(N2C(=O)c3csc(N)c3C2=O)C1=O]

48) 5-(1-(2-hydroxypropyl)-2,6-dioxopiperidin-3-yl)-1-amino-5H-thieno(3,4-c)pyrrole-4,6-dione

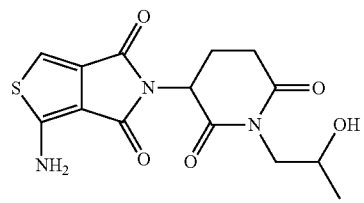 [SMILES: CC(O)CN1C(=O)CCC(N2C(=O)c3csc(N)c3C2=O)C1=O]

49) 5-(1-(2-methoxypropyl-2,6-dioxopiperidin-3-yl)-1-amino-5H-thieno(3,4-c)pyrrole-4,6-dione

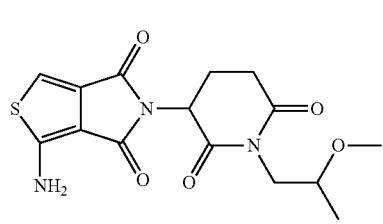 [SMILES: COC(C)CN1C(=O)CCC(N2C(=O)c3csc(N)c3C2=O)C1=O]

50) 5-(1-butyl-2,6-dioxopiperidin-3-yl)-1-amino-5H-thieno(3,4-c)pyrrole-4,6-dione

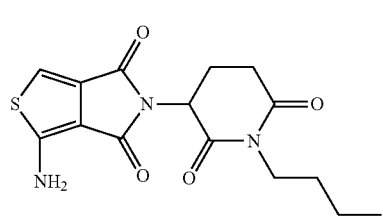 [SMILES: CCCCN1C(=O)CCC(N2C(=O)c3csc(N)c3C2=O)C1=O]

51) 5-(1-methyl-2,6-dioxopiperidin-3-yl)-1-methylamino-5H-thieno(3,4-c)pyrrole-4,6-dione

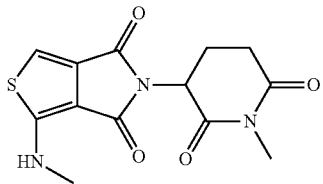 [SMILES: CNc1scc2c1C(=O)N(C1CCC(=O)N(C)C1=O)C2=O]

52) 5-(1-ethyl-2,6-dioxopiperidin-3-yl)-1-methylamino-5H-thieno(3,4-c)pyrrole-4,6-dione

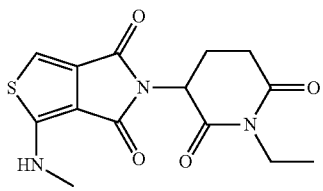 [SMILES: CCN1C(=O)CCC(N2C(=O)c3csc(NC)c3C2=O)C1=O]

53) 5-(1-(2-methoxypropyl)-2,6-dioxopiperidin-3-yl)-1-methylamino-5H-thieno(3,4-c)pyrrole-4,6-dione

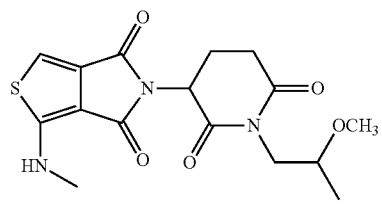 [SMILES: CNc1scc2c1C(=O)N(C1CCC(=O)N(CC(C)OC)C1=O)C2=O]

54) (R)-5-(3-methyl-1-ethyl-2,6-dioxopiperidin-3-yl)-1-amino-5H-thieno(3,4-c)pyrrole-4,6-dione

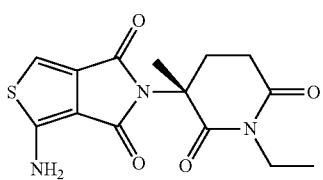 [SMILES: CCN1C(=O)CC[C@@](C)(N2C(=O)c3csc(N)c3C2=O)C1=O]

55) (S)-5-(3-methyl-1-ethyl-2,6-dioxopiperidin-3-yl)-1-amino-5H-thieno(3,4-c)pyrrole-4,6-dione

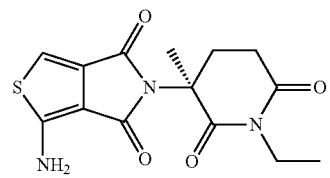 [SMILES: CCN1C(=O)CC[C@](C)(N2C(=O)c3csc(N)c3C2=O)C1=O]

56) (±)-5-(3-methyl-1-ethyl-2,6-dioxopiperidin-3-yl)-1-amino-5H-thieno(3,4-c)pyrrole-4,6-dione

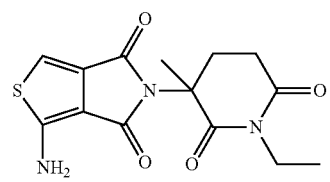

57) (R)-5-(3-methyl-1-propyl-2,6-dioxopiperidin-3-yl)-1-amino-5H-thieno(3,4-c)pyrrole-4,6-dione

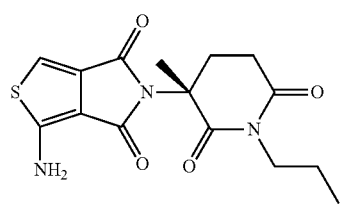 [SMILES: CCCN1C(=O)CC[C@@](C)(N2C(=O)c3csc(N)c3C2=O)C1=O]

58) (S)-5-(3-methyl-1-propyl-2,6-dioxopiperidin-3-yl)-1-amino-5H-thieno(3,4-c)pyrrole-4,6-dione

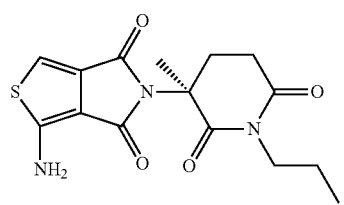 [SMILES: CCCN1C(=O)CC[C@](C)(N2C(=O)c3csc(N)c3C2=O)C1=O]

59) (±)-5-(3-methyl-1-propyl-2,6-dioxopiperidin-3-yl)-1-amino-5H-thieno(3,4-c)pyrrole-4,6-dione

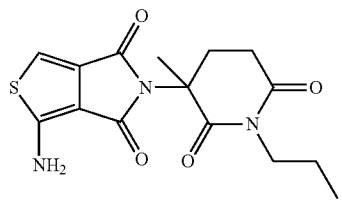 [SMILES: CCCN1C(=O)CCC(C)(N2C(=O)c3csc(N)c3C2=O)C1=O]

60) (R)-5-(3-methyl-1-(2-hydroxyethyl)-2,6-dioxopiperidin-3-yl)-1-amino-5H-thieno(3,4-c)pyrrole-4,6-dione

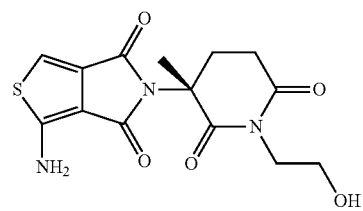 [SMILES: C[C@@]1(N2C(=O)c3csc(N)c3C2=O)CCC(=O)N(CCO)C1=O]

61) (S)-5-(3-methyl-1-(2-hydroxyethyl)-2,6-dioxopiperidin-3-yl)-1-amino-5H-thieno(3,4-c)pyrrole-4,6-dione

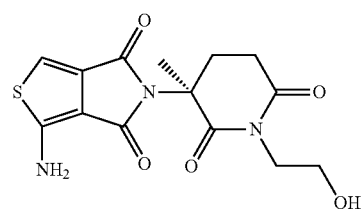 [SMILES: C[C@]1(N2C(=O)c3csc(N)c3C2=O)CCC(=O)N(CCO)C1=O]

62) (±)-5-(3-methyl-1-(2-hydroxyethyl)-2,6-dioxopiperidin-3-yl)-1-amino-5H-thieno(3,4-c)pyrrole-4,6-dione

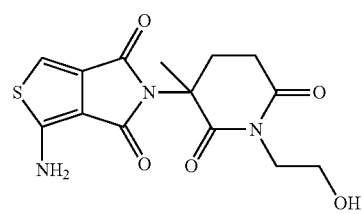

63) (R)-5-(3-methyl-1-(2-methoxyethyl)-2,6-dioxopiperidin-3-yl)-1-amino-5H-thieno(3,4-c)pyrrole-4,6-dione

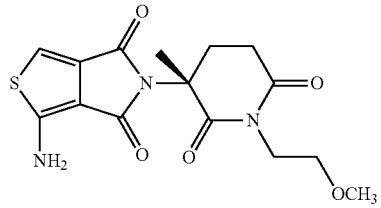 [SMILES: COCCN1C(=O)CC[C@@](C)(N2C(=O)c3csc(N)c3C2=O)C1=O]

64) (S)-5-(3-methyl-1-(2-methoxyethyl)-2,6-dioxopiperidin-3-yl)-1-amino-5H-thieno(3,4-c)pyrrole-4,6-dione

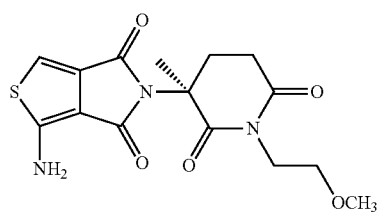 [SMILES: COCCN1C(=O)CC[C@](C)(N2C(=O)c3csc(N)c3C2=O)C1=O]

65) (±)-5-(3-methyl-1-(2-methoxyethyl)-2,6-dioxopiperidin-3-yl)-1-amino-5H-thieno(3,4-c)pyrrole-4,6-dione

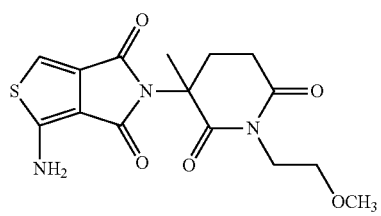 [SMILES: COCCN1C(=O)CCC(C)(N2C(=O)c3csc(N)c3C2=O)C1=O]

66) 5-(1-(methoxycarbonylmethyl)-2,6-dioxopiperidin-3-yl)-5H-thieno(3,4-c)pyrrole-4,6-dione

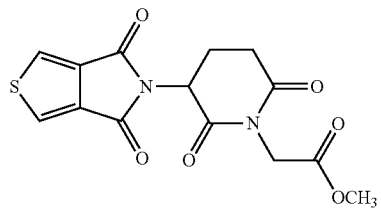 [SMILES: COC(=O)CN1C(=O)CCC(N2C(=O)c3cscc3C2=O)C1=O]

67) 5-(1-(ethoxycarbonylmethyl)-2,6-dioxopiperidin-3-yl)-5H-thieno(3,4-c)pyrrole-4,6-dione

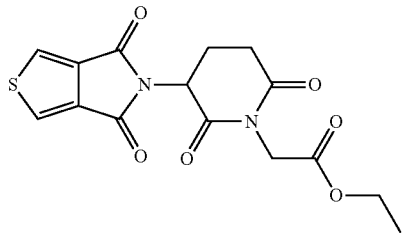 [SMILES: CCOC(=O)CN1C(=O)CCC(N2C(=O)c3cscc3C2=O)C1=O]

68) 5-(1-(methoxycarbonylmethyl)-2,6-dioxopiperidin-3-yl)-1-amino-5H-thieno(3,4-c)pyrrole-4,6-dione

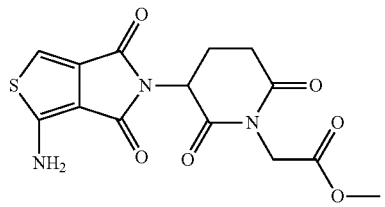 [SMILES: COC(=O)CN1C(=O)CCC(N2C(=O)c3csc(N)c3C2=O)C1=O]

69) 5-(1-(ethoxycarbonylmethyl)-2,6-dioxopiperidin-3-yl)-1-amino-5H-thieno(3,4-c)pyrrole-4,6-dione

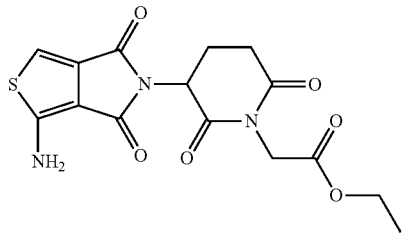 [SMILES: CCOC(=O)CN1C(=O)CCC(N2C(=O)c3csc(N)c3C2=O)C1=O]

70) 5-(1-(methoxycarbonylethyl)-2,6-dioxopiperidin-3-yl)-1-amino-5H-thieno(3,4-c)pyrrole-4,6-dione

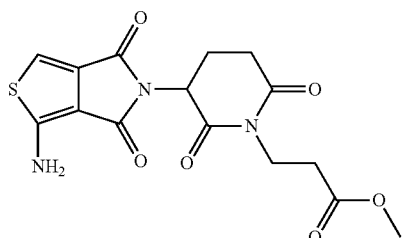

71) 5-(1-(ethoxycarbonylethyl)-2,6-dioxopiperidin-3-yl)-1-amino-5H-thieno(3,4-c)pyrrole-4,6-dione

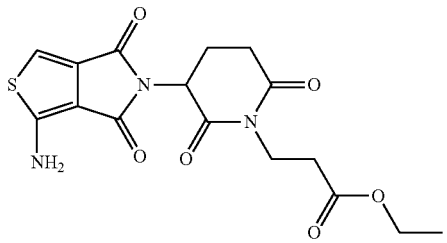 [SMILES: CCOC(=O)CCN1C(=O)CCC(N2C(=O)c3csc(N)c3C2=O)C1=O]

72) 5-(1-(methoxycarbonylethyl)-2,6-dioxopiperidin-3-yl)-1-amino-5H-thieno(3,4-c)pyrrole-4,6-dione

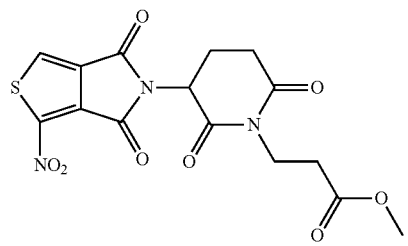 [SMILES: COC(=O)CCN1C(=O)CCC(N2C(=O)c3csc([N+](=O)[O-])c3C2=O)C1=O]

73) 5-(1-(methoxycarbonylmethyl)-2,6-dioxopiperidin-3-yl)-1-nitro-5H-thieno(3,4-c)pyrrole-4,6-dione

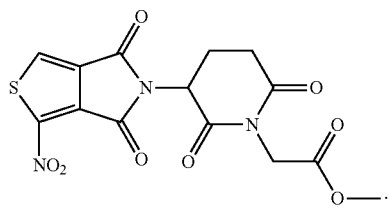 [SMILES: COC(=O)CN1C(=O)CCC(N2C(=O)c3csc([N+](=O)[O-])c3C2=O)C1=O]

As a natural extension, this invention also includes various metabolites and prodrugs of the compounds encompassed by formula (I).

When used as pharmaceutically-active ingredients, the compounds encompassed by formula (I) may be R isomers, S isomers, or racemates.

When used as pharmaceutically-active ingredients, the compounds encompassed by formula (I) may be in the form of a free base, or a physiologically-acceptable inorganic salt, including a hydrochlorate, a sulphate, a nitrate, or a phosphate, or an organic salt, including a sulphonate, an acetate, a formate, a fumarate, a maleate, a citrate, a tartrate, a malate, an ascorbate, a gluconate, a lactate, a succinate, or a trifluoroacetate.

When used as pharmaceutically-active ingredients, the compounds encompassed by formula (I) may be in the form of a hydrate of a free base.

When used as pharmaceutically-active ingredients, the compounds encompassed by formula (I) may be in the form of a hydrate of a physiologically-acceptable salt.

This invention is directed further to a first method for preparing a 5H-thioeno(3,4-c)pyrrole-4,6-dione derivative encompassed by formula (I), comprising reacting a compound of formula (II) with a compound of formula (III)

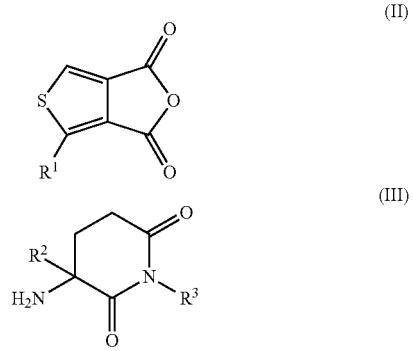

to yield an intermediate, and then converting said intermediate in a ring-closure reaction to the 5H-thioeno(3,4-c)pyrrole-4,6-dione derivative, wherein $R^1$ represents H, $C_{1-6}$alkyl, $OR^4$, $OC(O)R^5$, $NO_2$, $NHC(O)R^6$, or $NR^7R^8$;

$R^2$ represents H, a halogen, or $C_{1-6}$alkyl;

$R^3$ represents H, methyl, isopropyl, allyl, benzyl, $CH_2CO_2$($C_{1-6}$alkyl), or $CH_2(CH_2)_nR^9$;

$R^4$, $R^5$, $R^6$, $R^7$, and $R^8$ represent independently and at each occurrence H, or $C_{1-6}$alkyl;

$R^9$ represents H, $C_{1-6}$ alkyl, OH, $OC_{1-6}$alkyl, $NH_2$, $NHC_{1-6}$alkyl, $N(C_{1-6}$alkyl$)_2$, or $CO_2(C_{1-6}$alkyl); and n represents 1, 2, 3, or 4.

In more detail, this method comprises the following steps:

step 1: reacting a compound represented by formula (II) with a compound represented by formula (III) to obtain a compound represented by formula (IVA) or formula (IVB);

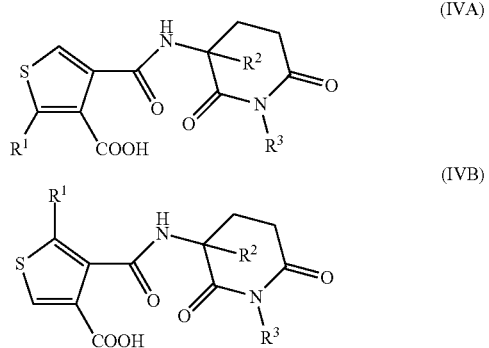

step 2: reacting the compound represented by formula (IVA) or formula (IVB) with a condensing agent in an aprotic solvent to obtain a compound represented by formula (I).

After step 1, the obtained product, i.e., the compound represented by formula (IVA) or formula (IVB), may be purified or may be used without purification. The reaction mixture obtained after step 1 may be dried to remove water. Step 1 and 2 may be conducted in situ (merged into one step).

In step 1, the mol proportion between the amount of the compound represented by formula (II) to that of the compound represented by formula (III) is between 1.0:0.4 and 1.0:2.0; more particularly, between 1.0:0.6 and 1.0:1.5; and most particularly, between 1.0:0.8 and 1.0:1.2.

One or more organic bases and/or inorganic bases, including but not limited to triethylamine, trimethylamine, pyridine, NaOH, KOH, LiOH, $Ca(OH)_2$, $Na_2CO_3$, $K_2CO_3$, $Cs_2CO_3$, $NaHCO_3$, $KHCO_3$, $Na_3PO_4$, $Na_2HPO_4$, $NaH_2PO_4$, $K_3PO_4$, $K_2HPO_4$, $KH_2PO_4$, or a mixtures thereof, may be added to the reaction mixture in step 1, in step 2, and/or if the steps are conducted in situ.

All reactions described herein is performed, without limitation, in an organic solvent, such as dichloromethane, chloroform, acetone, butanone, N,N-dimethylformamide, dimethyl sulfoxide, dimethoxyethane, tetrahydrofuran, pyridine, and acetonitrile; and the reaction mixture may be monophasic, biphasic, or multiphasic, with or without the addition of phase transfer catalysts.

In step 2, the condensing agents appropriate for the preparation of compounds shown as formula (I) include, but are not limited to carbonyldiimidazole, DCC, EDC, $SOCl_2$, $PCl_5$, $POCl_3$, or acetic anhydride, or their mixture. In step 2, the ratio of the molar amount of the condensing agent to the molar amount of the compound represented by formula (II) may be between 0.5:1.0 and 4.0:1.0; particularly, between 0.8:1.0 and 3.0:1.0; and more particularly between 1.0:1.0 and 1.5:1.0.

The appropriate solvents for step 2 include, but are not limited to DMF, DMA, DMSO, HMPA, THF, ethyl acetate, isopropyl ether, acetone, dimethoxyethane, diethylene glycol diethyl ether, 1,4-dioxane, chlorobenzene, nitrobenzene, acetonitrile, or their mixture.

The temperature of the reaction mixture in step 2 may be maintained at between 0° C. and 200° C.; more particularly at between 10° C. and 150° C., and most particularly at between 15° C. and 100° C.

When preparing the compound of formula (I) by this method, in step 1 and/or step 2, a pyridine derivative may be added as a catalyst. The pyridine derivative is selected pyridine, 4-dimethylaminopyridine, 4-diethylaminopyridine, or 4-(1'-tetrahydropyrryl)pyridine. The molar ratio of the pyridine derivative to the compound of formula (II) is between 0.1 and 20 percent.

This invention is directed further to a second method for preparing a 5H-thioeno(3,4-c)pyrrole-4,6-dione derivative encompassed by formula (I) comprising reacting a compound represented by formula (V)

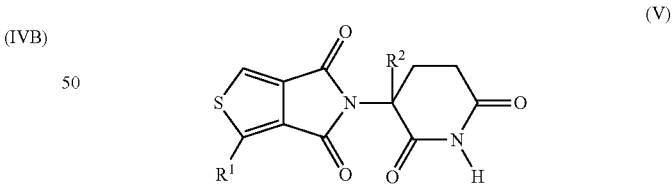

with a compound represented by formula X—$R^3$ in the presence of a base to yield a 5H-thioeno(3,4-c)pyrrole-4,6-dione derivative represented by formula (I), wherein, $R^1$ represents H, $C_{1-6}$alkyl, $OR^4$, $OC(O)R^5$, $NO_2$, $NHC(O)R^6$, or $NR^7R^8$;

$R^2$ represents H, a halogen, or $C_{1-6}$alkyl;

$R^3$ represents methyl, isopropyl, allyl, benzyl, $CH_2CO_2$($C_{1-6}$alkyl), or $CH_2CH_2R^9$;

$R^9$ represents H, $C_{1-6}$ alkyl, OH, $OC_{1-6}$alkyl, $NH_2$, $NHC_{1-6}$alkyl, $N(C_{1-6}$alkyl$)_2$, or $CO_2(C_{1-6}$alkyl); and X represents a leaving group, such as Cl, Br, I, Ms, Ts, and so on.

The base is selected from an inorganic base including, but are not limited to NaH, KH, CaH$_2$, K$_2$CO$_3$, Na$_2$CO$_3$, KHCO$_3$, NaHCO$_3$, Li$_2$CO$_3$, Cs$_2$CO$_3$, LiOH, KOH, NaOH, Ca(OH)$_2$, K$_3$PO$_4$, or K$_2$HPO$_4$, or an organic base. The molar ratio of the base to the compound represented by formula (V) is between 50% and 300%.

The reaction is performed, without limitation, in an organic solvent, such as dichloromethane, chloroform, acetone, butanone, N,N-dimethylformamide, dimethyl sulfoxide, dimethoxyethane, tetrahydrofuran, pyridine and acetonitrile; and the reaction mixture may be monophasic, biphasic, or multiphasic, with or without the addition of phase transfer catalysts.

This invention is directed further to a method for preparing a 5H-thioeno(3,4-c)pyrrole-4,6-dione derivative represented by formula (I), wherein R$^1$ represents an amino group,

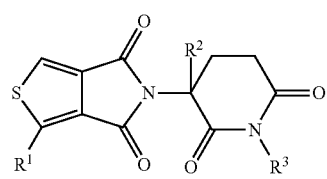

(I)

comprising reducing a compound represented by formula (I) in a reduction reaction,
wherein R$^1$ represents a nitryl to yield a compound represented by formula (I), wherein R$^1$ represents an amino. The reduction reaction for reducing nitryl may be a catalytic hydrogenation.

Appropriate reaction solvents include, but are not limited to water, alcohols, DMF, DMA, DMSO, HMPA, THF, dimethoxyethane, diethylene glycol diethyl ether, 1,4-dioxane, chlorobenzene, nitrobenzene, acetonitrile, or their mixture.

The pressure range of hydrogen used in the hydrogenation reaction is between 1 and 200 times the atmospheric pressure.

The temperature range for this reaction is between $-30°$ C. and $180°$ C.

The catalyst employed may be a metal such as Pd, Pt, Ru, Ni, etc, their oxides, their salts, or their mixture.

During this reaction, acid may be added.

Further, the reduction reaction for reducing the nitryl in the 5H-thioeno(3,4-c)pyrrole-4,6-dione derivatives represented by formula (I) may employ a reducing agent selected from a non-metal salt; a hydride, such as borohydride; a metallic salt, such as tin protochloride; or a reducing metal and a hydrogen source, such as zerovalent iron powder and a protic acid.

The reaction solvents include, but are not limited to water, an alcohol, DMF, DMA, DMSO, HMPA, THF, dimethoxyethane, diethylene glycol diethyl ether, 1,4-dioxane, benzene, toluene, acetonitrile, or their mixture.

The temperature range for this reaction is between $-30°$ C. and $180°$ C.

Compounds of formula (I) are useful pharmaceutically-active ingredients for treating or preventing diseases which may be effectively alleviated or cured by decreasing TNFα levels in the human body, including but not limited to inflammatory, infectious, immune or maglinant tumor diseases; and particularly, sepsic shock, endotoxin-related shock, hemodynamic shock, sepsis, post ischemic reperfusion injury, malaria, mycobacterial infection, meningitis, psoriasis, congestive heart failure, fibrotic disease, cachexia, transplantation immune rejection, cancer, autoimmune disease, opportunistic infection in AIDS, erythema nodosum leprosum, lupus erythematosus, incurable lupus erythematosus, Behcet's Syndrome, regional ileitis, myelodysplastic syndrome, rheumatoid arthritis (RA), hepatitis, nephritis, rheumatoid spondylitis, multiple myeloma, thyroma, kidney cancer, prostatic carcinoma, lymphoma, leukemia, and liver cancer.

The invention is directed further to pharmaceutical compositions comprising at least one compound represented by formula (I) and a diluent, excipient, loading agent, solvent, colorant, and/or adhesive. The selection of adjuvants and dosage is decided by a skilled artisan taking into account the mode of administration, e.g., gastrointestinal, intravenous, abdominal, dermal, intramuscular, nasal, ocular, pulmonary, anal, vaginal, transdermal, etc.

When used as pharmaceutically-active ingredients, the compounds represented by formula (I) may be made into a rapid release, slow release, and common medicament forms.

When used as pharmaceutically-active ingredients, the dose of the compounds represented by formula (I) depends on administration routines, administration strategies, disease types, detailed condition of patients, etc.

When used as pharmaceutically-active ingredients, the compounds represented by formula (I) may be formulated in combination with other appropriate pharmaceutically-active compounds.

DETAILED DESCRIPTION OF THE INVENTION

Examples

Pharmacological Research: Effects of Monocyte (PBMC) Stimulation by LPS on TNFα

Cytokine TNFα released by PBMCs in the peripheral blood after lipid polysaccharide (LPS) stimulation in vitro was studied. The followings are experimental protocols for studying cytokine TNFα released by PBMCs, which are inhibited by compounds of the invention.

PBMCs were obtained from blood of at least three volunteers after heparin treatment, using gradient extraction. PBMCs were collected and washed three times with a 1640 medium (10% calf serum, 2 mM L-glutamine, 100 mM mercaptoethanol, 50 μg/mL streptomycin, 50 U/mL penicillin), then placed into wells of a 24-well cell culture plate. The concentration was adjusted to $1 \times 10^6$ cells/mL with 1640 culture medium. Test compounds, as shown in Table 1, were dissolved in dimethylsulfoxide at a given concentration. The resultant solution was added to the cell culture medium and the culture plate was placed in a CO$_2$ incubator (5% CO$_2$, 90% humidity) for 1 hour. Then, LPS (Sigma) was added and its concentration was adjusted to 0.1 μg/mL (except for the control).

After a 20 hr incubation period, the content of TNFα in supernatant of the above PBMC culture medium was assayed by ELISA kit (America Genzyme Co), using standard method. The measured value of the control well (not treated with active components), and the measured value of the test wells containing the test compounds was used to calculate the TNFα inhibition rate. The concentration of compounds giving a 50% TNFα inhibition (IC$_{50}$ value) was calculated using nonlinear regression analysis. Each concentration was determined twice and an average value was calculated. Results are illustrated in Table 1.

TABLE 1

Activity of Inhibition of TNFα Release from Monocytes Stimulated by LPS

| Compound | Test Concentration (μM) | Degree of inhibition (%) | IC$_{50}$ (μM) |
|---|---|---|---|
| Neurosedyn | 100 | 22 | 183 |
| Example 10 | 100 | 32 | |
| Example 13 | 100 | 20 | |
| Example 15 | 100 | 18 | |
| Example 16 | 100 | 28 | |
| Example 18 | 100 | 28 | |
| Example 19 | 3.0 | 95 | 0.006 |
| Example 22 | 3.0 | 62 | 0.5 |
| Example 24 | 3.0 | 48 | |
| Example 27 | 3.0 | 84 | 0.050 |
| Example 31 | 3.0 | 71 | 0.350 |

Abbreviations

CDI: carbonyl diimidazole; DCM: dichloromethane; TFA: trifluoroacetic acid; CDCl$_3$: deuterochloroform; DMAP: 4-(N,N-dimethylamino)pyridine; TEA: triethylamine; DMF: N,N-dimethylformamide; DMSO: dimethyl sulfoxide.

Example 1

Thiophene-3,4-dicarbonitrile

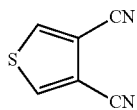

To a 2000 mL three-necked flask under inert gas, equipped with a mechanic stirrer, and a reflux condenser, 96.80 g of 3,4-dibromothiophene, 104 g cuprous cyanide, and 100 mL anhydrous DMF were added. After refluxing for 4 h, the reaction mixture was cooled down to room temperature; and a solution obtained by dissolving 400 g of FeCl$_3$.6H$_2$O in 700 mL of hydrochloric acid (1.7 M) was added into the reaction mixture and allowed to react for 30 min at 60-70° C. After the reaction mixture was fully cooled, 500 mL DCM was added. The reaction mixture was divided into 300 mL portions and extracted with DCM (2×300 mL). The DCM layers were combined. The extracts were divided into 600 mL portions, washed successively with 2×50 mL 6N hydrochloric acid, water, saturated Na$_2$CO$_3$ aq., and brine; dried over anhydrous MgSO$_4$, filtered, and evaporated to dryness to obtain a yellow solid. The solid was washed with a mixture of ethyl acetate:petroleum ether=1:1, and filtered to obtain a white solid (21 g). $^1$H NMR (CDCl$_3$): δ 8.07 (s, 2H).

Example 2

Thiophene-3,4-dicarboxylic acid

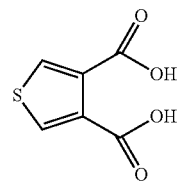 [SMILES: O=C(O)c1cscc1C(=O)O]

To a 500 mL round bottom flask equipped with an electromagnetic stirrer and a reflux condenser, 15.978 g of 3,4-dicyanothiophene, 43.997 g KOH, and 174 mL glycol were added; and the mixture was refluxed for 4 h. After the reaction mixture was cooled, 350 mL water was added, and the aqueous layer was extract with ether (2×100 mL). The layers were separated, the aqueous layer was cooled down in an ice bath, and excess strong hydrochloric acid was added until a white precipitate appeared. The solid was filtered and dissolved in 2000 mL of ether. The aqueous layer was extracted with ether (3×300 mL). Organic layers were combined, dried over anhydrous MgSO$_4$, filtered, and evaporated to dryness. 15 g of white solid was obtained and recrystallized from water. $^1$H NMR (DMSO-d$_6$): δ 10.35 (brs, 2H, COOH), 8.17 (s, 2H); MS (m/z): 171 (M−1)$^+$.

Example 3

Thieno(3,4-c)furan-1,3-dione

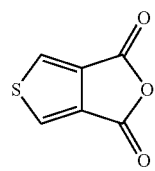

To a 250 mL round bottom flask under inert atmosphere, equipped with an electromagnetic stirrer, and a reflux condenser, 15 g of thieno-3,4-dicarboxylic acid and 120 mL of acetic anhydride were added. The mixture was refluxed for 3 h, evaporated to dryness to remove solvent. 13 g of deep brown solid were obtained.

Example 4

2-nitrothiophene-3,4-dicarboxylic acid

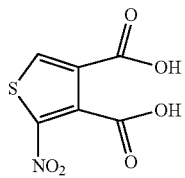

To a 250 mL round bottom flask under inert atmosphere, equipped with an electromagnetic stirrer, 40 mL of fuming nitric acid (95%) were added. The flask was cooled down to between 0 and 5° C. 10 g of thieno(3,4-c)furan-1,3-dione was added in portions (1 g at a time), and then the mixture was allowed to react for 30 min while maintaining the temperature. A yellow solid precipitated out. The reaction mixture was poured into 80 g ice water mixture, and extracted with ethyl acetate (3×100 mL). Organic layers were combined, washed with water (2×50 mL) and brine, dried over anhydrous MgSO₄, filtered, and evaporated to dryness to remove the solvent. A yellow solid (10 g) was obtained. MS (m/z): 216 (M−1)⁺.

Example 5

4-nitrothieno(3,4-c)furan-1,3-dione

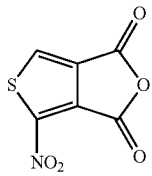

To a 250 mL round bottom flask under inert atmosphere equipped with an electromagnetic stirrer, 10 g of 2-nitrylthieno-3,4-dicarbonyl acid and 100 mL of acetic anhydride were added. The mixture was stirred for 3 h, evaporated to dryness to remove the solvent, and a deep brown solid (9 g) was obtained.

Example 6

Benzyl 2,6-dioxopiperidin-3-yl carbamate

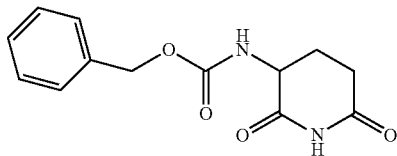 [SMILES: O=C1CCC(NC(=O)OCc2ccccc2)C(=O)N1]

11.2 g of CBZ-L-glutamine was dissolved in 120 mL anhydrous THF. 7.776 g of CDI and a catalytic quantity of DMAP were added to the above solution, and the reaction mixture was refluxed for 6 h. After cooling, the reaction mixture was filtered to remove a small quantity of insoluble substances, evaporated to dryness to remove THF, and recrystallized from ethyl acetate to obtain a white solid (8.5 g). ¹H NMR (CDCl₃): δ 8.37 (s, 1H), 7.36-7.26 (m, 5H, Ph), 5.67 (d, 1H, J=3 Hz), 5.14 (s, 2H), 4.40-4.33 (m, 1H), 2.82-2.67 (m, 2H), 2.58-2.49 (m, 1H), 1.96-1.85 (m, 1H).

Example 7

3-aminopiperidine-2,6-dione

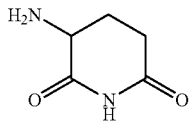

7.86 g of benzyl 2,6-dioxopiperidin-3-yl carbamate were dissolved in 30 mL of THF and 30 mL of methanol. 0.786 g of 10% Pd/C were added to the above solution. The reaction mixture was allowed to react under a flow of hydrogen at room temperature for 2 h, filtered to remove the catalyst, and evaporated to dryness to remove the solvent. A light blue solid (3.818 g) was obtained.

Example 8

Tert-butyl 2,6-dioxopiperidin-3-yl carbamate

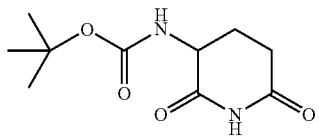 [SMILES: CC(C)(C)OC(=O)NC1CCC(=O)NC1=O]

11.4 g BOC-L-glutamine were dissolved in 120 mL of anhydrous THF. 7.776 g of CDI and a catalytic quantity of DMAP was added to the solution. The reaction mixture was refluxed and reacted for 6 h. After being cooled, the reaction mixture was filtered to remove a small quantity of insoluble substances, evaporated to dryness to remove THF, and recrystallized with ethyl acetate to obtain a white solid (4.5 g). ¹H NMR (DMSO-d₆): δ 7.15 (d, 1H, J=3 Hz), 4.26-4.19 (m, 1H), 2.76-2.67 (m, 1H), 2.49-2.47 (m, 1H), 2.01-1.91 (m, 2H).

Example 9

3-aminopiperidine-2,6-dione trifluoroacetic acid

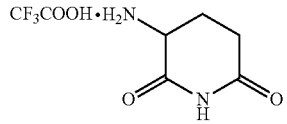

2.28 g of tert-butyl 2,6-dioxopiperidin-3-yl carbamate was suspended in 30 mL of DCM, and 10 mL TFA was added. The reaction mixture was stirred at room temperature for 4 h, and was evaporated to dryness to remove the solvent. 2.4 g of a solid were obtained.

Example 10

5-(2,6-dioxopiperidin-3-yl)-5H-thieno(3,4-c)pyrrole-4,6-dione (Method 1)

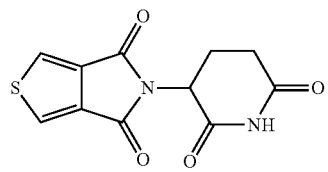 [SMILES: O=C1CCC(N2C(=O)c3cscc3C2=O)C(=O)N1]

To a 250 mL round bottom flask equipped with an electromagnetic stirrer, 14.6 g of glutamine, 60 mL of water, and 60 mL of TFA were added. When glutamine fully dissolved, the reaction mixture was cooled on an ice bath to between 0 and 5° C., and 15.4 g of theino(3,4-c)furan-1,3-dione was added. At the above temperature, the reaction mixture was allowed to react for 30 min. The reaction mixture was then allowed to warm to room temperature and allowed to react for additional 4 h. The reaction mixture was stripped of solvent in vacuo at 85° C. over 4 h to obtain a tacky solid (28 g). The solid was dissolved in 140 mL of anhydrous THF, and 20 g of CDI and a catalytic quantity of DMAP were added and allowed to react at a reflux for 6 h until a large amount of white solid precipitated. The white solid was cooled and filtered to yield 18 g of dried title compound. ¹H NMR (DMSO-d₆): δ 11.10 (s, 1H), 8.26 (s, 2H), 5.03 (dd, 1H, J=3 Hz, J=3 Hz), 2.87-2.82 (m, 1H), 2.66-2.55 (m, 2H), 2.07-2.04 (m, 1H); MS (m/z): 263 (M−1)⁺.

Example 11

5-(2,6-dioxopiperidin-3-yl)-5H-thieno(3,4-c)pyrrole-4,6-dione (Method 2)

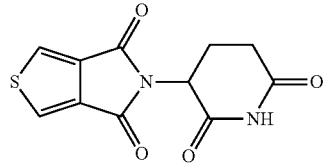

1.54 g thieno(3,4-c)furan-1,3-dione was dissolved in 20 mL of anhydrous THF, and 12.8 g of 3-aminopiperidine-2,6-dione was added. The reaction mixture was allowed to react at room temperature for 4 h. Then, 2 g of CDI and a catalytic quantity of DMAP were added, and the reaction mixture was allowed to reflux for 6 h until a large amount of white solid precipitated. The solid was cooled and filtered to yield 2.1 g of the title product.

Example 12

5-(2,6-dioxopiperidin-3-yl)-5H-thieno(3,4-c)pyrrole-4,6-dione (Method 3)

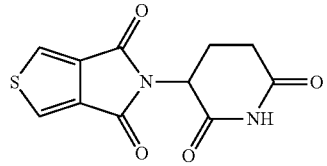 [SMILES: O=C1CCC(N2C(=O)c3cscc3C2=O)C(=O)N1]

1.54 g thieno(3,4-c)furan-1,3-dione and 1.42 g of 3-aminopiperidine-2,6-dione trifluoroacetic acid were dissolved in 15 mL of acetic acid. The reaction mixture was refluxed overnight, cooled, and evaporated to remove the solvent. The residue was dissolved in 20 mL anhydrous THF, and 2 g of CDI, and a catalytic quantity of DMAP were added. The reaction mixture was refluxed for 6 h until a large amount of white solid precipitated. The solid was cooled and filtered to yield 1.9 g of the title compound.

Example 13

5-(1-methyl-2,6-dioxopiperidin-3-yl)-5H-thieno(3,4-c)pyrrole-4,6-dione

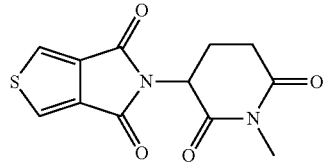 [SMILES: CN1C(=O)CCC(N2C(=O)c3cscc3C2=O)C1=O]

0.264 g of 5-(2,6-dioxopiperidin-3-yl)-5H-thieno(3,4-c)pyrrole-4,6-dione were dissolved in 10 mL anhydrous DMF, and 0.036 g of NaH (95%) were added. The reaction mixture was reacted at room temperature for 30 min, and 0.2 mL of CH₃I were added. The reaction mixture was allowed to stir overnight. 100 mL of water were added, and the aqueous phase was extracted with ethyl acetate (3×30 mL). Organic phases were combined, washed with 30 mL of water and 30 mL of brine, dried over anhydrous MgSO₄, filtered, and evaporated to dryness. A white solid (0.196 g) was obtained. ¹H NMR (CDCl₃): δ 7.91 (s, 2H), 4.93 (d, 1H, J=3 Hz), 3.22 (s, 3H), 3.04-2.94 (m, 1H), 2.83-2.71 (m, 2H), 2.11 (m, 1H); MS (m/z): 278 (M)⁺.

Example 14

5-(1-propyl-2,6-dioxopiperidin-3-yl)-5H-thieno(3,4-c)pyrrole-4,6-dione

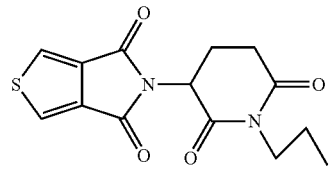 [SMILES: CCCN1C(=O)CCC(N2C(=O)c3cscc3C2=O)C1=O]

Methyl iodide was replaced with bromopropane and the reaction procedure of example 13 was repeated to obtain 0.215 g of a white solid. ¹H NMR (CDCl₃): δ 7.89 (s, 2H), 4.93-4.88 (m, 1H), 3.80-3.75 (m, 2H), 2.98-2.94 (m, 1H), 2.76-2.71 (m, 2H), 2.11-2.08 (m, 1H), 1.62-1.53 (m, 2H), 0.90 (t, 1H, J=6 Hz); MS (m/z): 305 (M−1)⁺.

Example 15

5-(1-methoxycarbonyl-2,6-dioxopiperidin-3-yl)-5H-thieno(3,4-c)pyrrole-4,6-dione

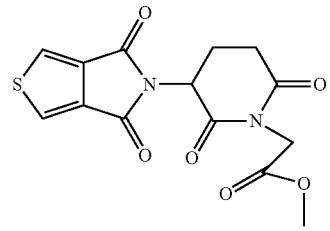 [SMILES: COC(=O)CN1C(=O)CCC(N2C(=O)c3cscc3C2=O)C1=O]

Methyl iodide was replaced with methyl bromoacetate and the reaction procedure of example 13 was repeated to obtain 0.238 g of a white solid. ¹H NMR (CDCl₃): δ 7.90 (s, 2H), 5.06-5.03 (m, 1H), 4.57 (s, 2H), 3.74 (s, 3H), 3.80-3.75 (m, 2H), 3.04-2.97 (m, 1H), 2.90-2.77 (m, 2H), 2.14-2.05 (m, 1H).

Example 16

5-(1-(2-methoxyethyl)-2,6-dioxopiperidin-3-yl)-5H-thieno(3,4-c)pyrrole-4,6-dione

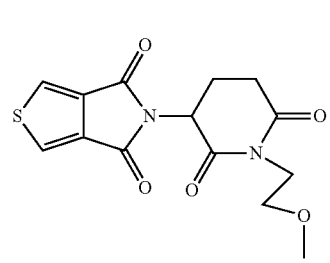 [SMILES: COCCN1C(=O)CCC(N2C(=O)c3cscc3C2=O)C1=O]

Methyl iodide was replaced with 2-bromoethyl methyl ether and the reaction procedure of example 13 was repeated to obtain 0.214 g of a white solid. $^1$H NMR (CDCl$_3$): δ 7.90 (s, 2H), 4.97-4.93 (m, 1H), 4.13-3.95 (m, 2H), 3.53 (t, 2H, J=4 Hz), 3.34 (s, 3H), 2.99-2.93 (m, 1H), 2.82-2.70 (m, 2H), 2.10 (m, 1H); MS (m/z): 321 (M−1)$^+$.

Example 17

5-(1-(3-hydroxypropanyl)-2,6-dioxopiperidin-3-yl)-5H-thieno(3,4-c)pyrrole-4,6-dione

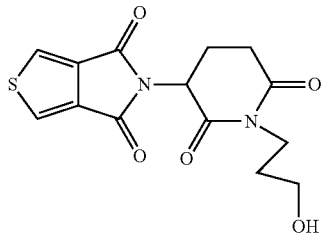 [SMILES: O=C1CCC(N2C(=O)c3cscc3C2=O)C(=O)N1CCCO]

Methyl iodide was replaced with 3-bromopropanol and the reaction procedure of example 13 was repeated to obtain a white solid. MS (m/z): 321 (M−1)$^+$.

Example 18

1-nitro-5-(2,6-dioxopiperidin-3-yl)-5H-thieno(3,4-c)pyrrole-4,6-dione

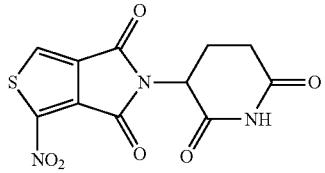

1.99 g of 2-nitrylthieno(3,4-c)furan-1,3-dione was dissolved in 20 mL anhydrous THF, and 1.28 g of 3-aminopiperidine-2,6-dione were added. The reaction mixture was allowed to react at room temperature for 4 h, and 2 g of DCI and a catalytic quantity of DMAP were added. The reaction mixture was refluxed for 6 h until a deep brown solid precipitated. The mixture was cooled and filtered to obtain 1.6 g of the title compound. $^1$H NMR (DMSO-d$_6$): δ 11.17 (s, 1H), 8.68 (s, 1H), 5.14 (dd, 1H, J=3 Hz, J=3 Hz), 2.91-2.83 (m, 1H), 2.62-2.45 (m, 2H), 2.06-1.99 (m, 1H).

Example 19

1-amino-5-(2,6-dioxopiperidin-3-yl)-5H-thieno(3,4-c)pyrrole-4,6-dione (Method 1)

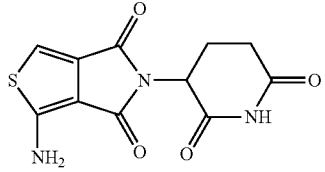

0.309 g of 1-nitro-5-(2,6-dioxopiperidin-3-yl)-5H-thieno (3,4-c)pyrrole-4,6-dione was dissolved in 40 mL of THF, and 0.309 g of 10% Pd/C were added. The reaction mixture was reacted under an atmosphere of hydrogen at room temperature for 4 h, filtered to remove the catalyst, evaporated to dryness. The reaction mixture was purified by silica gel column chromatography to obtain the title compound as a solid (0.108 g). $^1$H NMR (DMSO-d$_6$): δ 11.00 (s, 1H), 7.62 (s, 2H), 7.19 (s, 1H), 4.91 (dd, 1H, J=3 Hz, J=3 Hz), 2.89-2.73 (m, 1H), 2.58-2.40 (m, 2H), 1.99-1.91 (m, 1H); MS (m/z): 278 (M−1)$^+$.

Example 20

1-amino-5-(2,6-dioxopiperidin-3-yl)-5H-thieno(3,4-c)pyrrole-4,6-dione (Method 2)

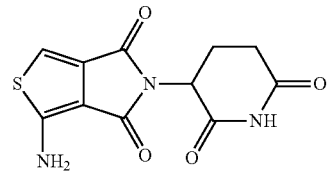

0.309 g of 1-nitro-5-(2,6-dioxopiperidin-3-yl)-5H-thieno (3,4-c)pyrrole-4,6-dione was dissolved in 10 mL of acetone, and a solution obtained by dissolving 0.783 g Na$_2$S$_2$O$_4$ in 10 mL water was added. The reaction mixture was refluxed for 2 h, cooled, and 10 mL of water were added. The aqueous phase was extracted with ethyl acetate (3×50 mL). The organic phases were combined, washed with 40 mL of water and 40 mL of brine, dried over anhydrous MgSO$_4$, filtered, evaporated to dryness. The remaining residue was purified on silica gel column chromatography to obtain a solid (0.145 g).

Example 21

1-amino-5-(2,6-dioxopiperidin-3-yl)-5H-thieno(3,4-c)pyrrole-4,6-dione (Method 3)

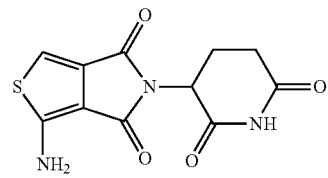

0.309 g of 1-nitryl-5-(2,6-dioxopiperidin-3-yl)-5H-thieno (3,4-c)pyrrole-4,6-dione was suspended in 20 mL of ethanol and 20 mL of water, and 0.7 g freshly-activated iron powder (washed with water after hydrochloric acid treatment) and 5 mL acetic acid were added and refluxed for 2 h. The reaction mixture was cooled and filtered. The filtered solution was evaporated to dryness; and the remaining residue was dissolved in 150 mL of ethyl acetate, washed with 40 mL of water and 40 mL of brine, dried over anhydrous MgSO$_4$, filtered, and evaporated to dryness. The remaining residue was purified on silica gel column chromatography to obtain a solid (0.095 g).

Example 22

1-methylamino-5-(2,6-dioxopiperidin-3-yl)-5H-thieno(3,4-c)pyrrole-4,6-dione

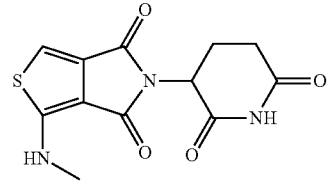 [SMILES: CNc1scc2c1C(=O)N(C1CCC(=O)NC1=O)C2=O]

0.084 g of 1-amino-5-(2,6-dioxopiperidin-3-yl)-5H-thieno(3,4-c)pyrrole-4,6-dione was dissolved in 10 mL of DMF, and 0.5 mL of methyl iodide were added. The reaction mixture was heated to 80° C., allowed to react at that temperature for 6 h, cooled, and 100 mL of water were added. The reaction solution was extracted with ethyl acetate (3×30 mL). The organic phases were combined, washed with 30 mL of and 30 mL of brine, dried over anhydrous MgSO₄, filtered, and evaporated to dryness. The remaining residue was purified on silica gel column chromatography to yield a solid (0.033 g). MS (m/z): 292 (M−1)⁺.

Example 23

1-dimethylamino-5-(2,6-dioxopiperidin-3-yl)-5H-thieno(3,4-c)pyrrole-4,6-dione

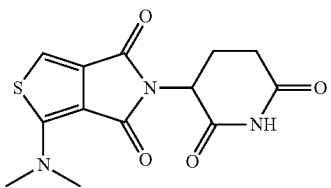 [SMILES: CN(C)c1scc2c1C(=O)N(C1CCC(=O)NC1=O)C2=O]

0.084 g of 1-amino-5-(2,6-dioxopiperidin-3-yl)-5H-thieno(3,4-c)pyrrole-4,6-dione was dissolved in 10 mL of DMF, and 0.5 mL of methyl iodide was added. The reaction mixture was heated to 80° C., reacted at that temperature for 6 h, cooled, and then 100 mL of water were added. The reaction mixture was extracted with ethyl acetate (3×30 mL). The organic phases were combined, washed with 30 mL of water, and 30 mL of brine, dried over anhydrous MgSO₄, filtered, and evaporated to dryness. The remaining residue was purified on silica gel column chromatography to obtain a solid (0.024 g). MS (m/z): 308 (M+1)⁺.

Example 24

1-acetamido-5-(2,6-dioxopiperidin-3-yl)-5H-thieno(3,4-c)pyrrole-4,6-dione

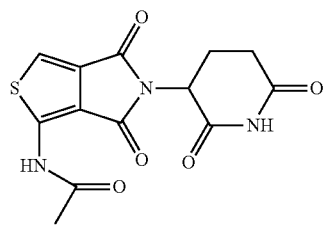 [SMILES: CC(=O)Nc1scc2c1C(=O)N(C1CCC(=O)NC1=O)C2=O]

0.084 g 1-amino-5-(2,6-dioxopiperidin-3-yl)-5H-thieno(3,4-c)pyrrole-4,6-dione was dissolved in 10 mL of acetic anhydride and refluxed for 6 h. The reaction mixture was cooled and evaporated to dryness. The remaining residue was purified on silica gel column chromatography to yield a solid (0.067 g). MS (m/z): 320 (M−1)⁺.

Example 25

5-(3-methyl-2,6-dioxopiperidin-3-yl)-5H-thieno(3,4-c)pyrrole-4,6-dione

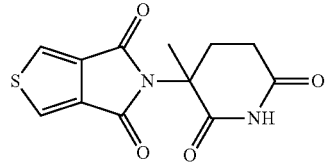 [SMILES: CC1(N2C(=O)c3cscc3C2=O)CCC(=O)NC1=O]

1.54 g of thieno(3,4-c)furan-1,3-dione was dissolved in 20 mL of anhydrous THF, and 1.42 g of 3-amino-3-methylpiperidin-2,6-dione was added. The reaction mixture was allowed to react at room temperature for 4 h, and 2 g of CDI and a catalytic quantity of DMAP were added. The reaction mixture was allowed to reflux for 6 h during which time a solid precipitated. The reaction solution was cooled and filtered to obtain a white solid (2.2 g). MS (m/z): 278 (M)⁺.

Example 26

1-nitro-5-(3-methyl-2,6-dioxopiperidin-3-yl)-5H-thieno(3,4-c)pyrrole-4,6-dione

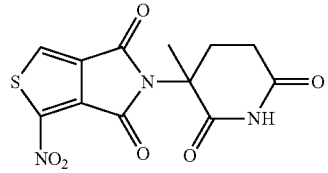

1.99 g of 2-nitrothieno(3,4-c)furan-1,3-dione was dissolved in 20 mL of anhydrous THF, and 1.42 g of 3-amino-3-dioxopiperidin-2,6-dione (prepared by a method described in *Bioorg. Med. Chem. Lett.* 1999, 9, 1625.) was added. The reaction mixture was allowed to react at room temperature for 4 h, and 2 g of CDI and a catalytic quantity of DMAP were added. The reaction mixture was refluxed for 6 h during which time a solid precipitated. The reaction solution was cooled and filtered to obtain a white solid (1.5 g). MS (m/z): 322 (M−1)⁺.

Example 27

1-amino-5-(3-methyl-2,6-dioxopiperidin-3-yl)-5H-thieno(3,4-c)pyrrole-4,6-dione

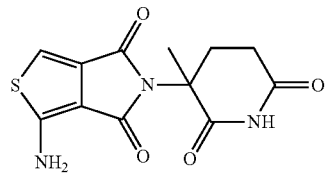

0.323 g of 1-nitro-5-(3-methyl-2,6-dioxopiperidin-3-yl)-5H-thieno(3,4-c)pyrrole-4,6-dione was dissolved in 10 mL of acetone, and a solution obtained by dissolving 0.783 g Na₂S₂O₄ in 100 mL of water was added. The reaction mixture was refluxed for 2 h, cooled, and 100 mL of water were added. The aqueous phase was extracted with ethyl acetate (3×50 mL), the organic phases were combined and washed with 40 mL of water and 40 mL of brine, dried over anhydrous MgSO₄, filtered, and evaporated to dryness. The remaining residue was purified on silica gel column chromatography to obtain a solid (0.156 g). MS (m/z): 292 (M−1)⁺.

Example 28

Tert-butyl 1-methyl-2,6-dioxopiperidin-3-yl carbamate

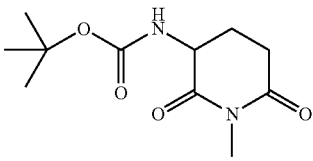 [SMILES: CN1C(=O)CCC(NC(=O)OC(C)(C)C)C1=O]

0.228 g of tert-butyl 2,6-dioxopiperidin-3-yl carbamate was dissolved in 10 mL of DMF, and 0.036 g of NaH (95%) were added. The reaction mixture was allowed to react at room temperature for 30 min, and 0.2 mL of CH₃I were added. The reaction mixture was allowed to react overnight. Then, 100 mL of water were added and the aqueous phase was extracted with ethyl acetate (3×30 mL). The organic phases were combined and washed with 30 mL of water and 30 mL of brine, dried over anhydrous MgSO₄, filtered, and evaporated to dryness. The remaining residue was purified on silica gel column chromatography to yield a solid (0.186 g).

Example 29

1-methyl 3-aminopiperidine-2,6-dione trifluoroacetic acid

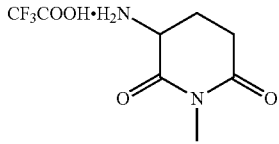

0.242 g of tert-butyl 1-methyl-2,6-dioxopiperidin-3-yl carbamate was dissolved in 10 mL of DCM, and 3 mL of TFA were added. Then, the mixture was stirred at room temperature for 4 h. The reaction mixture was evaporated to dryness, and a solid was obtained (0.253 g).

Example 30

1-nitro-5-(1-methyl-2,6-dioxopiperidin-3-yl)-5H-thieno(3,4-c)pyrrole-4,6-dione

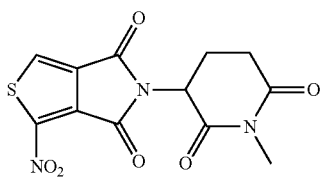

0.199 g of 2-nitrothieno(3,4-c)furan-1,3-dione was dissolved in 20 mL of anhydrous THF, and 0.256 g of 1-methyl-3-aminopiperidin-2,6-dione trifluoroacetate and 0.1 mL of TFA were added. The reaction mixture was allowed to react at room temperature for 4 h, and then 0.2 g of CDI and a catalytic quantity of DMAP were added. The reaction mixture was allowed to react for 6 h, cooled and evaporated to dryness. The remaining residue was dissolved in 80 mL of ethyl acetate, washed successively with 40 mL of 1N HCl, 40 mL of water, and 40 mL of brine, dried over anhydrous MgSO₄, filtered, and evaporated to dryness. The remaining residue was separated on silica gel column chromatography to yield a solid (0.103 g). MS (m/z): 322 (M−1)⁺.

Example 31

1-amino-5-(1-methyl-2,6-dioxopiperidin-3-yl)-5H-thieno(3,4-c)pyrrole-4,6-dione

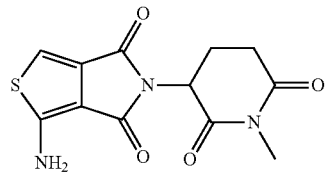

0.097 g of 1-nitro-5-(1-methyl-2,6-dioxopiperidin-3-yl)-5H-thieno(3,4-c)pyrrole-4,6-dione was dissolved in 10 mL of acetone; and a solution obtained by dissolving 0.239 g of Na₂S₂O₄ in 10 mL of water was added. The reaction mixture was refluxed for 2 h, cooled, and 10 mL of water were added. The aqueous phase was extracted with ethyl acetate (3×30 mL), the organic phases were combined, washed with 40 mL of water and 40 mL of brine, dried over anhydrous MgSO₄, filtered, and evaporated to dryness to remove the solvent. The remaining residue was purified on silica gel column chromatography to yield a solid (0.046 g). MS (m/z): 292 (M−1)⁺.

The invention claimed is:
1. A method of decreasing tumor necrosis factor-alpha levels in blood of a patient in need thereof, the method comprising administering to the patient a compound represented by formula (I),

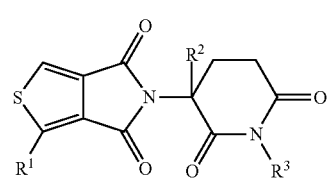

an organic salt thereof, or an inorganic salt thereof, wherein
$R^1$ represents H, $NO_2$, $NHC(O)R^6$, or $NR^7R^8$;
$R^2$ represents H or $CH_3$;
$R^3$ represents H, methyl, isopropyl, allyl, benzyl, $CH_2CO_2(C_{1-6}alkyl)$, or $CH_2(CH_2)_nR^9$;
$R^6$, $R^7$, and $R^8$ each independently and at each occurrence represent H, or $C_{1-6}$ alkyl;
$R^9$ represents H, $C_{1-6}$alkyl, OH, $C_{1-6}$alkyloxy, $NH_2$, $C_{1-6}$ alkylamino, $N(C_{1-6}alkyl)_2$, or $CO_2(C_{1-6}alkyl)$; and
n represents 1, 2, 3, or 4.

2. The method of claim 1, wherein the compound or an organic or inorganic salt thereof is administered by a mode of administration selected from gastrointestinal, oral, intravenous, abdominal, dermal, intramuscular, nasal, ocular, pulmonary, anal, vaginal, or transdermal.

3. The method of claim 1, wherein the compound or an organic or inorganic salt thereof is administered in combination with other active pharmaceutical compounds.

4. The method of claim 1, wherein $R^1$ represents H, $NO_2$, $NH_2$, $NHCH_3$, $NHCH_2CH_3$, $N(CH_3)_2$, or $NHCOCH_3$.

5. The method of claim 1, wherein $R^3$ represents H, methyl, ethyl, propyl, 2-hydroxyethyl, 3-hydroxyethyl, 2-methoxyethyl, methoxycarbonylmethyl, or ethoxycarbonylmethyl.

6. The method of claim 1, wherein the compound is 1-amino-5-(3-methyl-2,6-dioxopiperidin-3-yl)-5H-thieno(3,4-c)pyrrole-4,6-dione.

7. The method of claim 1, wherein the compound is
   (a) 1-amino-5-(3-methyl-2,6-dioxopiperidin-3-yl)-5H-thieno(3,4-c)pyrrole-4,6-dione,
   (b) 5-(2,6-dioxopiperidin-3-yl)-5H-thieno(3,4-c)pyrrole-4,6-dione,
   (c) 5-(1-methyl-2,6-dioxopiperidin-3-yl)-5H-thieno(3,4-c)pyrrole-4,6-dione,
   (d) 5-(1-propyl-2,6-dioxopiperidin-3-yl)-5H-thieno(3,4-c)pyrrole-4,6-dione,
   (e) 5-(1-methoxycarbonylmethyl-2,6-dioxopiperidin-3-yl)-5H-thieno(3,4-c)pyrrole-4,6-dione,
   (f) 5-(1-(2-methoxyethyl)-2,6-dioxopiperidin-3-yl)-5H-thieno(3,4-c)pyrrole-4,6-dione,
   (g) 5-(1-(3-hydroxypropyl)-2,6-dioxopiperidin-3-yl)-5H-thieno(3,4c)pyrrole-4,6-dione,
   (h) 1-nitro-5-(2,6-dioxopiperidin-3-yl)-5H-thieno(3,4-c)pyrrole-4,6-dione,
   (i) 1-amino-5-(2,6-dioxopiperidin-3-yl)-5H-thieno(3,4-c)pyrrole-4,6-dione,
   (j) 1-methylamino-5-(2,6-dioxopiperidin-3-yl)-5H-thieno(3,4-c)pyrrole-4,6-dione,
   (k) 1-dimethylamino-5-(2,6-dioxopiperidin-3-yl)-5H-thieno(3,4-c)pyrrole-4,6-dione,
   (l) 1-acetamido-5-(2,6-dioxopiperidin-3-yl)-5H-thieno(3,4-c)pyrrole-4,6-dione,
   (m) 5-(3-methyl-2,6-dioxopiperidin-3-yl)-5H-thieno(3,4-c)pyrrole-4,6-dione,
   (n) 1-nitro-5-(3-methyl-2,6-dioxopiperidin-3-yl)-5H-thieno(3,4-c)pyrrole-4,6-dione,
   (o) 1-nitro-5-(1-methyl-2,6-dioxopiperidin-3-yl)-5H-thieno(3,4-c)pyrrole-4,6-dione, or
   (p) 1-amino-5-(1-methyl-2,6-dioxopiperidin-3-yl)-5H-thieno(3,4-c)pyrrole-4,6-dione.

8. The method of claim 1 wherein the patient has a disease selected from the group consisting of endotoxin-related shock, sepsis, post ischemic reperfusion injury, fatal hyperacute neurogenic syndrome brainstem-type malaria, cachexia, bone marrow transplantation immune rejection, opportunistic infection in AIDS, erythema nodosum leprosum, systemic lupus erythematosus, Behcet's syndrome, regional ileitis, myelodysplastic syndrome, rheumatoid arthritis, hepatitis, multiple myeloma, thyroma, kidney cancer, prostatic carcinoma, leukemia, and liver cancer.

9. The method of claim 8, wherein the disease is selected from the group consisting of systemic lupus erythematosus, regional ileitis, rheumatoid arthritis, septic shock, fatal hyperacute neurogenic syndrome brainstem-type malaria, opportunistic infection in AIDS, and hepatitis.

10. The method of claim 9, wherein the disease is regional ileitis.

11. A method of inhibiting release of tumor necrosis factor-alpha in monocytes stimulated by lipid polysaccharide in vitro, the method comprising adding to the monocytes a compound represented by formula (I),

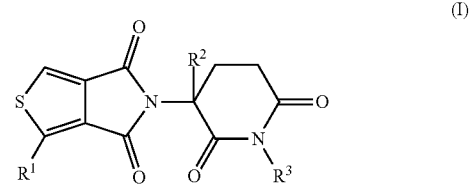

(I)

an organic salt thereof, or an inorganic salt thereof, wherein
$R^1$ represents H, $NO_2$, $NHC(O)R^6$, or $NR^7R^8$;
$R^2$ represents H or $CH_3$;
$R^3$ represents H, methyl, isopropyl, allyl, benzyl, $CH_2CO_2(C_{1-6}alkyl)$, or $CH_2(CH_2)_nR^9$;
$R^6$, $R^7$, and $R^8$ each independently and at each occurrence represent H, or $C_{1-6}$ alkyl;
$R^9$ represents H, $C_{1-6}$alkyl, OH, $C_{1-6}$alkyloxy, $NH_2$, $C_{1-6}$alkylamino, $N(C_{1-6}alkyl)_2$, or $CO_2(C_{1-6}alkyl)$; and
n represents 1, 2, 3, or 4.

* * * * *